United States Patent
Hamdan

(10) Patent No.: US 8,406,871 B2
(45) Date of Patent: Mar. 26, 2013

(54) METHODS AND SYSTEMS FOR TREATING CARDIAC ARRHYTHMIAS

(75) Inventor: Mohamed Hussein Hamdan, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 333 days.

(21) Appl. No.: 12/709,433

(22) Filed: Feb. 19, 2010

(65) Prior Publication Data
US 2010/0217342 A1    Aug. 26, 2010

Related U.S. Application Data

(63) Continuation-in-part of application No. 12/393,014, filed on Feb. 25, 2009, now Pat. No. 8,285,374.

(51) Int. Cl.
*A61N 1/00* (2006.01)
(52) U.S. Cl. .......................................................... 607/4
(58) Field of Classification Search .................. 607/4
See application file for complete search history.

(56) References Cited

U.S. PATENT DOCUMENTS

| | | | |
|---|---|---|---|
| 5,184,615 | A | 2/1993 | Nappholz et al. |
| 7,206,633 | B2 | 4/2007 | Saba |
| 2003/0204209 | A1 | 10/2003 | Burnes |
| 2004/0002741 | A1* | 1/2004 | Weinberg ................. 607/17 |
| 2004/0172067 | A1 | 9/2004 | Saba |
| 2004/0215258 | A1 | 10/2004 | Lovett et al. |
| 2005/0149125 | A1* | 7/2005 | Kim et al. ................. 607/5 |
| 2006/0259082 | A1 | 11/2006 | Youker et al. |
| 2007/0038255 | A1 | 2/2007 | Kieval et al. |
| 2008/0147138 | A1 | 6/2008 | Maskara et al. |
| 2008/0177340 | A1 | 7/2008 | Kim et al. |
| 2008/0200960 | A1 | 8/2008 | Libbus |

OTHER PUBLICATIONS

Hamdan, et al., "Baroreflex Gain Predicts Blood Pressure Recovery During Simulated Ventricular Tachycardia in Humans", Circulation, Jul. 27, 1999, pp. 381-386.
Smith, et al. "Reflex Control of Sympathetic Activity During Simulated Ventricular Tachycardia in Humans", Circulation, Aug. 10, 1999, pp. 628-634.
Hamdan, et al., "Effect of P-Wave Timing During Supraventricular Tachycardia on the Hemodynamic and Sympathetic Neural Response", Circulation, Jan. 2-9, 2001, pp. 96-101.
Wasmund, et al., "Modulation of the Sinus Rate During Ventricular Fibrillation", Journal of Cardiovascular Electrophysiology, Feb. 2009, pp. 187-192, vol. 20, No. 2.

* cited by examiner

*Primary Examiner* — Christopher D Koharski
*Assistant Examiner* — Philip Edwards
(74) *Attorney, Agent, or Firm* — James W. Hill; McDermott Will & Emery LLP

(57) ABSTRACT

The disclosure includes methods and systems for treating cardiac arrhythmias. Some methods for treating an abnormal heart rhythm include determining a change in a sinus node cycle length of a heart of a patient between a time prior to the abnormal heart rhythm and a time during the abnormal heart rhythm; when the change is within a first range, delivering a first therapy to the patient for treating the abnormal heart rhythm; and when the change is within a second range, delivering a second therapy to the patient for treating the abnormal heart rhythm, wherein the first therapy is different from the second therapy. In some embodiments, the first therapy may include shock therapy and the second therapy may include anti-tachycardia pacing.

22 Claims, 17 Drawing Sheets

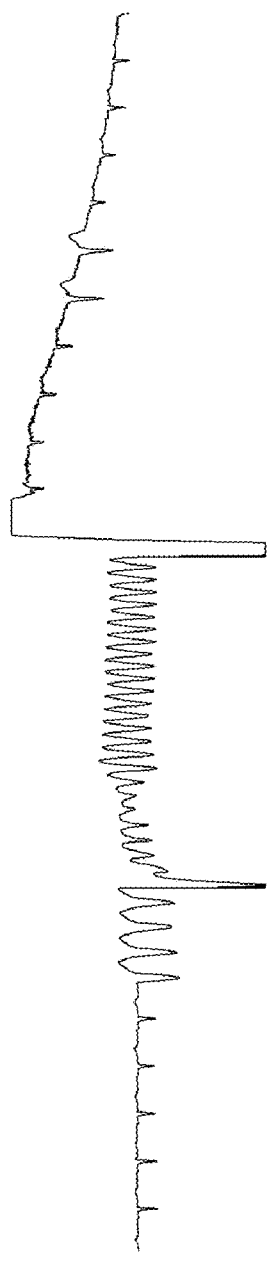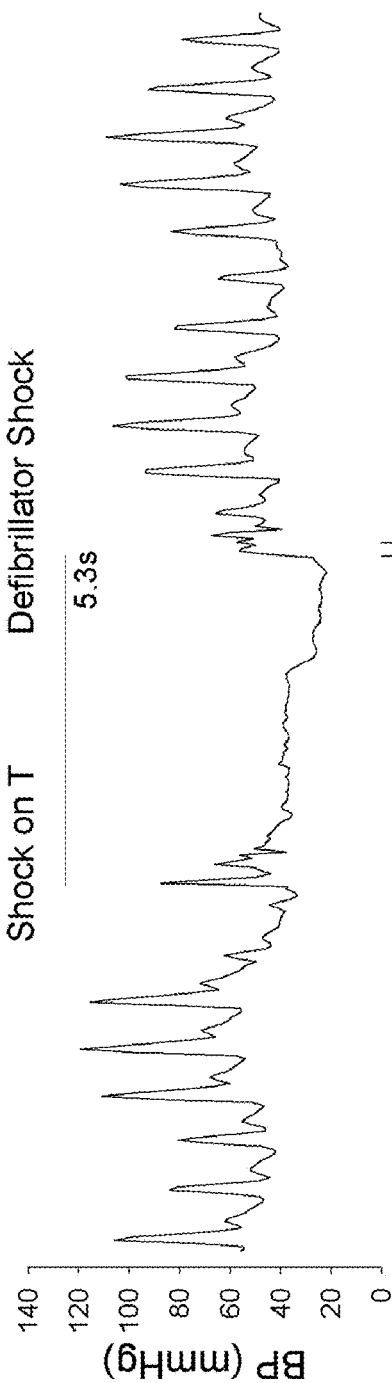
FIG. 11A
FIG. 11B
FIG. 11C

METHODS AND SYSTEMS FOR TREATING CARDIAC ARRHYTHMIAS

RELATED APPLICATION

This application is a continuation-in-part of application Ser. No. 12/393,014, titled "METHODS AND SYSTEMS FOR TREATING VENTRICULAR ARRHYTHMIAS," filed on Feb. 25, 2009.

FIELD OF THE INVENTIONS

The disclosure relates generally to systems and methods for cardiac complications, and in particular to systems and methods for treating cardiac arrhythmias.

BACKGROUND OF THE INVENTIONS

Cardiac defibrillators are medical devices for treating patients who have experienced an episode of ventricular tachycardia or ventricular fibrillation. Cardiac defibrillators are often implanted within a patient to detect and treat ventricular tachycardia or ventricular fibrillation. Implantable cardioverter-defibrillators (ICDs) include a small battery-powered electrical impulse generator that is implanted in patients who are at risk of developing ventricular fibrillation. The ICDs are programmed to detect cardiac arrhythmia and correct it by delivering a jolt of electricity through electrodes that are introduced into the heart.

ICDs can keep a record of the heart's activity when an abnormal heart rhythm occurs. With this information, an electrophysiologist can study the heart's activity and ask about other symptoms that may have occurred. Sometimes the ICD can be programmed to pace the heart to restore its natural rhythm.

SUMMARY OF THE INVENTIONS

Described herein are systems and methods for treating cardiac arrhythmias. Some embodiments described herein relate to a method of treating a fast ventricular arrhythmia that includes determining a value of a parameter indicative of a rate of an intrinsic pacemaker of a heart of a patient experiencing a fast ventricular arrhythmia (FVA); if the value indicates the rate is about equal to or higher than a threshold, delivering a first therapy to the patient for terminating the FVA; and if the value indicates the rate is lower than the threshold, delivering a second therapy, different from the first therapy, to the patient for terminating the FVA.

In some embodiments, the rate is a depolarization rate. In some embodiments, the intrinsic pacemaker comprises the sinoatrial node of the patient. In certain embodiments, the parameter indicative of the rate comprises a sinus node cycle length. Some embodiments provide that the fast ventricular arrhythmia comprises ventricular tachycardia, and the ventricular tachycardia can has a cycle length equal to or less than about 240 ms.

In some embodiments, determining a value of a parameter indicative of a rate comprises analyzing an atrial electrogram of the patient. Some embodiments provide that determining a value of a parameter indicative of a rate is performed using an electrode positioned in the patient's heart. In certain embodiments, determining a value of a parameter indicative of a rate is performed using an electrode positioned in an atrium of the patient.

Some embodiments provide that the first therapy comprises a therapy that is relatively painless to the patient. In some embodiments, the first therapy comprises anti-tachycardia pacing. In some embodiments, the second therapy comprises at least one of defibrillation and electrical cardioversion. Some embodiments provide that the second therapy comprises defibrillation. In some embodiments, the first therapy comprises anti-tachycardia pacing, and the second therapy comprises at least one of defibrillation and electrical cardioversion.

In some embodiments, determining a value of a parameter indicative of a rate and the delivering steps, mentioned above, are performed by a device implanted in the patient. In some embodiments, wherein the parameter indicative of a rate comprises a sinus node cycle length. The first therapy can include anti-tachycardia pacing, and the second therapy can include at least one of defibrillation and electrical cardioversion. The determining a value of a parameter indicative of a rate and the delivering steps can be, with the above description, performed by a device implanted in the patient.

In some embodiments, if the value indicates the rate is lower than a threshold, some methods provide for delivering a third therapy that stimulates the patient's sympathetic nervous system. In certain embodiments, the third therapy is sufficient to raise an arterial blood pressure in the patient. Some embodiments provide that the third therapy is electrical. In some embodiments, the third therapy comprises delivery of a sympathetic or sympathomimetic agent to the patient.

Some embodiments, provide a method, of treating a fast ventricular arrhythmia, including determining a value of a parameter indicative of at least one of vagal activity and peripheral sympathetic activity in a patient experiencing a fast ventricular arrhythmia; if the value is in a range indicating the ventricular arrhythmia is more likely to terminate in response to a painless therapy than if the value is outside the range, delivering the painless therapy to the patient; and if the value is outside the range, delivering a second therapy, comprising least one of defibrillation and electrical cardioversion, to the patient.

In some embodiments, the painless therapy comprises anti-tachycardia pacing. Some embodiments provide that the determining a value of a parameter and the delivering steps are performed by a device implanted in the patient. In some embodiments, the parameter comprises an indicator of depolarization of an intrinsic pacemaker in the patient's heart. Some embodiments provide that the intrinsic pacemaker comprises the sinoatrial node of the patient. Some embodiments provide that the parameter indicative of the rate comprises a sinus node cycle length.

In some embodiments, determining a value of a parameter comprises analyzing an atrial electrogram of the patient. Some embodiments provide that the determining a value of a parameter is performed using an electrode positioned in the patient's heart. In some embodiments, determining a value of a parameter is performed using an electrode positioned in an atrium of the patient.

Some embodiments provide that the second therapy of the above-mentioned embodiments comprises defibrillation. In some embodiments, the parameter comprises a sinus node cycle length and the determining a value of a parameter and the delivering steps are performed by a device implanted in the patient.

Some embodiments describe an implantable cardiac device or system, for treating a fast ventricular arrhythmia. In some embodiments, the device and/or system can include a determining module that determines a value of a parameter indicative of a rate of an intrinsic pacemaker of a heart of a patient experiencing a fast ventricular arrhythmia (FVA) and a delivery module, programmed to deliver a first therapy for terminating the FVA to the patient if the value indicates the rate is about equal to or higher than a threshold, and to deliver a second therapy for terminating the FVA, different from the first therapy, to the patient if the value indicates the rate is lower than the threshold.

In some embodiments, the rate is a depolarization rate. In some embodiments, the parameter is indicative of a rate of the sinoatrial node of the patent. Some embodiments provide that the parameter comprises a sinus node cycle length. In some embodiments, at least one of the first and second therapies is electrical. In some embodiments, the determining module analyzes an atrial electrogram of the patient, and in some embodiments, the determining module uses information derived from a signal transmitted via an electrode, positioned in an atrium of the patient, to determine the parameter value.

Some embodiments of the device and/or system provide that the first therapy comprises anti-tachycardia pacing, and some embodiments provide that the second therapy comprises at least one of defibrillation and electrical cardioversion. In some embodiments, the second therapy comprises defibrillation. In certain embodiments, the first therapy comprises anti-tachycardia pacing, and the second therapy comprises defibrillation.

In certain embodiments, a method, of treating a fast ventricular arrhythmia, is described including determining a value of a parameter indicative of a rate of an intrinsic pacemaker of a heart of a patient experiencing a fast ventricular arrhythmia (FVA); if the value indicates the rate is about equal to or higher than a threshold, delivering an electrical therapy, having a first value of a therapy parameter, to the patient for terminating the FVA; and if the value indicates the rate is lower than the threshold, delivering the electrical therapy, having a second value of the therapy parameter, to the patient.

In some embodiments, the rate is a depolarization rate. In some embodiments, the therapy parameter comprises at least one of a pulse waveform, a pulse rate, a pulse amplitude, a pulse width, and a pulse interval. In certain embodiments, the intrinsic pacemaker comprises the sinoatrial node of the patient. In some embodiments, the parameter indicative of the rate comprises a sinus node cycle length. Some embodiments provide that the fast ventricular arrhythmia comprises ventricular tachycardia. In some embodiments, the ventricular tachycardia has a cycle length equal to or less than about 240 ms.

In some embodiments, determining a value of a parameter indicative of a rate of an intrinsic pacemaker comprises analyzing an atrial electrogram of the patient. In certain embodiments, determining a value of a parameter indicative of a rate of an intrinsic pacemaker is performed using an electrode positioned in the patient's heart. Some embodiments provide that determining a value of a parameter indicative of a rate of an intrinsic pacemaker is performed using an electrode positioned in an atrium of the patient.

In some embodiments, the first therapy comprises a therapy that is relatively painless to the patient. Some embodiments provide that the first therapy comprises anti-tachycardia pacing. In certain embodiments, the second therapy comprises at least one of defibrillation and electrical cardioversion. In some embodiments, the second therapy comprises defibrillation. In certain embodiments, the first therapy comprises anti-tachycardia pacing, and the second therapy comprises defibrillation. Some embodiments provide that determining a value of a parameter indicative of a rate of an intrinsic pacemaker and the delivering steps are performed by a device implanted in the patient.

Some embodiments described herein relate to a method, of treating a ventricular arrhythmia, that includes determining a change in a sinus node cycle length of a heart of a patient between a time prior to the ventricular arrhythmia and a time during the ventricular arrhythmia; when the change in the sinus node cycle length is within a first range, delivering a first therapy to the patient for treating the ventricular arrhythmia; and when the change in the sinus node cycle length is within a second range, delivering a second therapy to the patient for treating the ventricular arrhythmia, wherein the first therapy is different from the second therapy.

In some embodiments, the change within the first range corresponds to lengthening of the sinus node cycle length during the ventricular arrhythmia. In some embodiments, the change within the second range corresponds to shortening of the sinus node cycle length during the ventricular arrhythmia.

In some embodiments, the first therapy comprises at least one of defibrillation and electrical cardioversion, and the second therapy comprises anti-tachycardia pacing. In some embodiments, the first therapy comprises a first number of anti-tachycardia pacing (ATP) attempts, and the second therapy comprises a second number of ATP attempts, the second number being greater than the first number. In some embodiments, each of the ATP attempts comprises a sequence of pulses delivered to one or both ventricles of the patient. In some embodiments, the determining and the delivering are performed by a device implanted in the patient.

In some embodiments, the determining the change in the sinus node cycle length comprises determining a first mean sinus node cycle length within a first time window prior to the onset of the ventricular arrhythmia; determining a second mean sinus node cycle length within a second time window from the onset of the ventricular arrhythmia; and determining the change in the sinus node cycle length based on the first and second mean sinus node cycle lengths.

Some embodiments provide a method, of treating an abnormal heart rhythm, that includes determining a change in a parameter indicative of a sinus node cycle length of a heart of a patient between a time prior to the abnormal heart rhythm and a time during the abnormal heart rhythm; when the change in the parameter indicative of the sinus node cycle length is within a first range, delivering a first therapy to the patient for treating the abnormal heart rhythm; and when the change in the parameter indicative of the sinus node cycle length is within a second range, delivering a second therapy to the patient for treating the abnormal heart rhythm, wherein the first therapy is different from the second therapy.

In some embodiments, the change within the first range corresponds to lengthening of the sinus node cycle length during the abnormal heart rhythm. In some embodiments, the change within the second range corresponds a shortening of the sinus node cycle length during the abnormal heart rhythm. In some embodiments, the first therapy comprises at least one of defibrillation and electrical cardioversion, and the second therapy comprises anti-tachycardia pacing. In some embodiments, the first therapy comprises a first number of anti-tachycardia pacing (ATP) attempts, and the second therapy comprises a second number of ATP attempts, the second number being greater than the first number. In some embodiments, the determining and the delivering are performed by a device implanted in the patient.

Some embodiments provide an implantable cardiac device, for treating an abnormal heart rhythm, that includes a determining module that determines a change in a parameter indicative of a sinus node cycle length of a heart of a patient between a time prior to the abnormal heart rhythm and a time during the abnormal heart rhythm; and a delivery module, programmed to deliver a first therapy for treating the abnormal heart rhythm to the patient when the change in the parameter is within a first range, and to deliver a second therapy for treating the abnormal heart rhythm, different from the first therapy, to the patient when the change in the parameter is within a second range.

In some embodiments, the change within the first range corresponds to lengthening of the sinus node cycle length during the abnormal heart rhythm. In some embodiments, the change within the second range corresponds to shortening of the sinus node cycle length during the abnormal heart rhythm. In some embodiments, the first therapy comprises at least one of defibrillation and electrical cardioversion, and the second therapy comprises anti-tachycardia pacing. In some embodiments, the first therapy comprises a first number of anti-tachycardia pacing (ATP) attempts, and the second therapy comprises a second number of ATP attempts, the second number being greater than the first number.

Some embodiments provide a method, of treating an abnormal heart rhythm, that includes determining a change in a parameter indicative of a sinus node cycle length of a heart of a patient between a time prior to the abnormal heart rhythm and a time during the abnormal heart rhythm; and selecting, based on the change in the parameter indicative of the sinus node cycle length, at least one of a first therapy and a second therapy for treatment of the abnormal heart rhythm.

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

BRIEF DESCRIPTION OF THE DRAWINGS

General descriptions provided herein that implement various features of the disclosure will now be described with reference to the drawings. The drawings and the associated descriptions are provided to illustrate embodiments of the disclosure and not to limit the scope of the disclosure.

FIG. 11A depicts ECG recordings during VF induction in a patient undergoing an ICD implant.

FIG. 11B depicts BP recordings during VF induction in a patient undergoing an ICD implant.

FIG. 11C depicts SNA recordings during VF induction in a patient undergoing an ICD implant.

DESCRIPTION OF THE INVENTIONS

Figure 1:
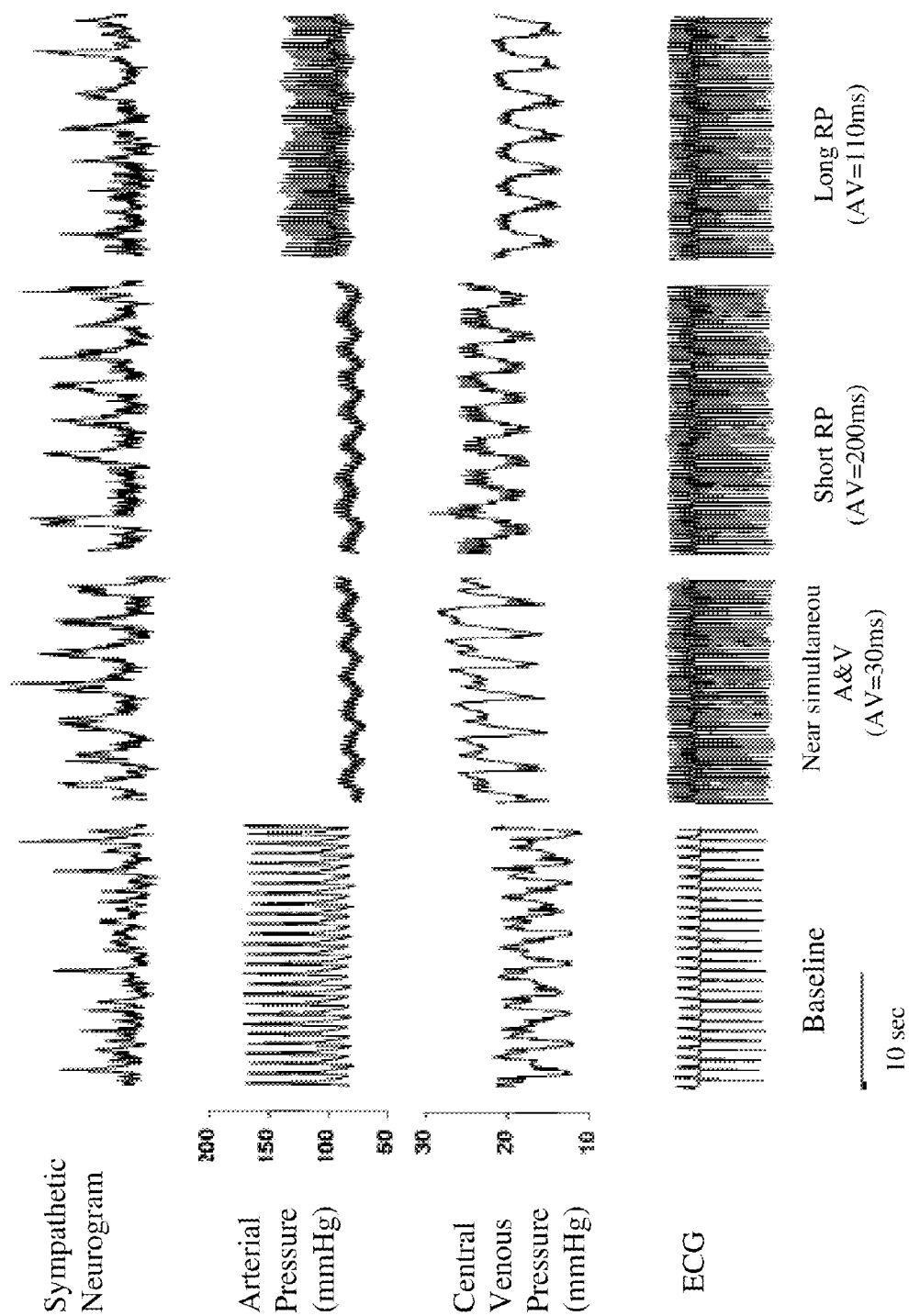
FIG. 1 depicts sample tracings of integrated sympathetic neurogram, arterial blood pressure, central venous pressure, and electrocardiogram during baseline and during rapid pacing in accordance with embodiments described herein.

The present disclosure provides systems and methods for treating cardiac arrhythmias. Some embodiments include an implantable cardiac device or system, for treating a fast ventricular arrhythmia. Certain embodiments can include a determining module that determines a value of a parameter indicative of a rate of an intrinsic pacemaker of a heart of a patient experiencing FVA. In some embodiments, for example, the rate can be a depolarization rate. Certain embodiments can include a delivery module, programmed to deliver a plurality of therapies to a patient experiences cardiac arrhythmia. A first therapy can be delivered, for terminating the FVA, to the patient if the value indicates the rate is about equal to or higher than a threshold. A second therapy, different from the first therapy, can be delivered to the patient if the value indicates the rate is lower than the threshold.

Some embodiments relate to a method of treating a fast ventricular arrhythmia that includes the step of determining a value of a parameter indicative of a rate of an intrinsic pacemaker of a heart of a patient experiencing a fast ventricular arrhythmia (FVA). In some embodiments, the rate is a depolarization rate. The method can provide treatment for a patient based on whether the rate is within a threshold or beyond such threshold. If the value indicates the rate is about equal to or higher than the threshold, the method provides for delivering a first therapy to the patient for terminating the FVA. If the value indicates the rate is lower than the threshold, the method provides for delivering a second therapy, different from the first therapy, to the patient for terminating the FVA.

In some embodiments, if the value indicates the rate is lower than a threshold, some methods provide for delivering a third therapy that stimulates the patient's sympathetic nervous system. In certain embodiments, the third therapy is sufficient to raise an arterial blood pressure in the patient. Some embodiments provide that the third therapy is electrical. In some embodiments, the third therapy comprises delivery of a sympathetic or sympathomimetic agent to the patient. In some embodiments, the third therapy is a combination of electrical and delivery of a sympathetic or sympathomimetic agent to the patient. In some embodiments, the agent may be delivered through an electrode that may be used for diagnostic or therapeutic purposes. Examples of additional drug delivery methods are know in the art and may be implemented accordingly. Examples of agents that can be used include epinephrine, phenylephrine, dopamine, etc.

In most circumstances, the application of painless therapy to fast ventricular arrhythmias (FVA; e.g., Cycle Length (CL) <240 ms) is limited by the inability to predict who is able to tolerate the arrhythmia without loss of consciousness. Described herein are tools to predict blood pressure response during FVA, thus enabling the application of painless therapy in patients who can tolerate it.

During simulated ventricular tachycardia (e.g., CL 240 ms), the arterial baroreflex plays a major role in mediating the sympathetic changes with minimal contribution from the cardiopulmonary baroreflex (Circulation. 1999 Aug. 10; 100(6): 628-34 (incorporated herein by reference)). Arterial baroreflex gain correlates with the blood pressure response (Circulation. 1999 Jul. 27; 100(4):381-6 (incorporated herein by reference)). In follow-up studies aimed at evaluating the role of the baroreflex in ventricular fibrillation (e.g., CL<240 ms), no correlations were found between arterial baroreflex gain and the changes in sinus node cycle length (SNCL). SNCL did not change and even lengthened in some patients, suggesting vagal activation and/or sympathoinhibition.

It has been observed that peripheral sympathetic activity decreased during induced ventricular fibrillation in a small number of patients. The lack of change, and even lengthening of the SNCL, combined with the finding of sympathoinhibition suggested that, in some patients, a "vasovagal"-like reaction could be taking place. During a vasovagal reaction, a paradoxical response occurs resulting in heart rate slowing, i.e., SNCL lengthening and sudden vasodilatation leading to a decrease in blood pressure. If this paradoxical response were to occur during FVA, the blood pressure response would be different in those with a vasovagal reaction when compared to those without a vasovagal reaction. By assessing the SNCL changes during the arrhythmia, it is possible to get an indication as to who will have a greater decrease in blood pressure and thus potentially an earlier loss of consciousness. The application of painless therapy in patients who develop of a vasovagal like reaction might be dangerous since they are more prone to lose consciousness earlier than those who do not develop a vasovagal like reaction. However, its use in patients without a vasovagal reaction might be beneficial, in that additionally treatment methodologies can be implemented. In some of these patients, successful painless therapy will prevent the delivery of painful shocks, thus improving the quality of life of patients with implantable defibrillators in addition to increasing battery longevity.

In conducting analysis of the possible "vasovagal" reaction it was found that: 1) SNCL did not change and even lengthened in a small number of animals; 2) the mechanism of the SNCL changes appeared to be vagally mediated; and 3) the percent decrease in blood pressure was greater in the animals with no SNCL changes or SNCL lengthening when compared to those with SNCL shortening. These findings were made from a limited number of studies.

It is also possible to distinguish the blood pressure response in patients without vasovagal reaction, i.e., those with SNCL shortening, by assessing the magnitude of the change in SNCL. The greater the SNCL shortening, the lesser the decrease in blood pressure, thus further improving the algorithm for painless therapy. No algorithm in place uses a device data to predict blood pressure response during ventricular arrhythmias. This disclosure will highlight what information should be looked at, and more importantly, will provide guidelines on how to use it in thousands of patients with devices.

Shock therapy has a major impact on the quality of life of thousands of patients with implantable defibrillators. While painless therapy has been shown to be effective in the treatment of ventricular arrhythmias with, for example, CL greater than about 240 ms, its application in the treatment of rapid ventricular arrhythmias with, for example, CL less than about 240 ms has been limited. The major concern has been the incidence of syncope. Proposed herein are new methods and systems that enable the identification of patients who can better tolerate painless therapy.

Simulated VT is associated with an increase in sympathetic nerve activity (SNA), and the magnitude of sympathoexcitation is correlated with arterial baroreflex gain. SNA recordings have not previously been obtained in patients during VF. In addition, the relationship between sinus node cycle length (SNCL) changes, and SNA during VF has not been evaluated.

In some methods, patients receiving dual chamber ICD implants with defibrillation threshold testing were asked to enroll. SNA recordings were attempted in all patients. In addition, the mean SNCL was measured during the 5 seconds preceding VF onset and the last 5 seconds before defibrillation. Seven patients were enrolled, and SNA measurements were successfully obtained in 3 patients. Atrial recordings were available in 6 patients. In patients with successful SNA recordings, sympathoinhibition was observed during VF in 2 patients, with sympathoexcitation noted in the remaining patient. Compared to baseline, SNCL shortened in 4 patients (−14% from baseline) and lengthened in the remaining 2 patients (+2% from baseline). In those with successful SNA recordings and SNCL measurements, the increase and decrease in SNA was associated with a reduction and lengthening in SNCL. These findings of sympathoinhibition associated with SNCL lengthening suggest the presence of vasovagal-like physiology during VF in a subgroup of patients. The implications regarding the magnitude of BP fall and application of painless therapy remain to be evaluated.

It has been shown in humans and in a porcine model that sinus node cycle length (SNCL) increases during VF in a significant number of cases, although it is uncertain what mechanism is responsible for the SNCL changes during VF. In eight anesthetized pigs, the chest was opened and the heart was exposed on a pericardial cradle. A 247-electrode sock was placed around the ventricles, an atrial lead over the right atrial appendage and an arterial catheter in the right femoral artery for blood pressure monitoring. Using DC current or the shock-on-T method, VF was induced and sustained for 30 seconds before applying a DC shock. Following a 10 minute recovery period, atropine (A, n=2) at 0.04 mg/kg, propranolol (P, n=2) at 0.2 mg/kg, both (A+P, n=2) or neither (Placebo, n=2) were administered at random, and VF was re-induced. SNCL changes were assessed before and after drug/placebo administration. Percent SNCL change (%ΔSNCL) was defined as %ΔSNCL=(VF−SNCL−Baseline−SNCL)/(Baseline−SNCL)*100. Atropine administration reversed the SNCL lengthening observed during VF while propranolol had little or no effect on SNCL shortening (see FIG. 9). The SNCL changes during the first 30 seconds of VF appear to be vagally mediated. The relationship between SNCL changes and peripheral sympathetic activity remain uncertain.

It has been shown that sinus node cycle length (SNCL) increases during VF in a significant number of cases. The relationship between SNCL changes and systemic BP remain unknown. In specific, whether SNCL lengthening is associated with peripheral sympathoinhibition and a greater decrease in BP, i.e., a vasovagal-like reaction is unclear. In test involving eleven anesthetized pigs, the chest was opened and the heart was exposed on a pericardial cradle. A 247-electrode sock was placed around the ventricles, an atrial lead over the right atrial appendage and an arterial catheter in the right femoral artery for blood pressure monitoring. Using DC current or the shock-on-T method, VF was induced and sustained for 30 seconds before applying a DC shock. Animals were divided in to 2 groups based on SNCL response during VF: Shortening group (n=7, %ΔSNCL=−17%), Lengthening group (n=4, %ΔSNCL=4%). RESULTS: In the Shortening group, mean BP fell by 53% in the first 10 sec. when compared to NSR and continued to fall to 64% and 68% at 20 sec. and 30 sec., respectively. In the Lengthening group, BP fell by 72%, 81% and 83% when compared to baseline. The differences in percent decrease in BP between the groups were statistically significant at all 3 time points during VF (p<0.05). SNCL lengthening was associated with a greater decrease in BP when compared to SNCL shortening. The above findings suggest that SNCL changes during VF might be helpful in predicting the magnitude of the hemodynamic fall in BP. Such information could be useful in deciding who has "time" for painless therapy before delivering shock therapy in patients with dual chamber ICDs.

Figure 10A:
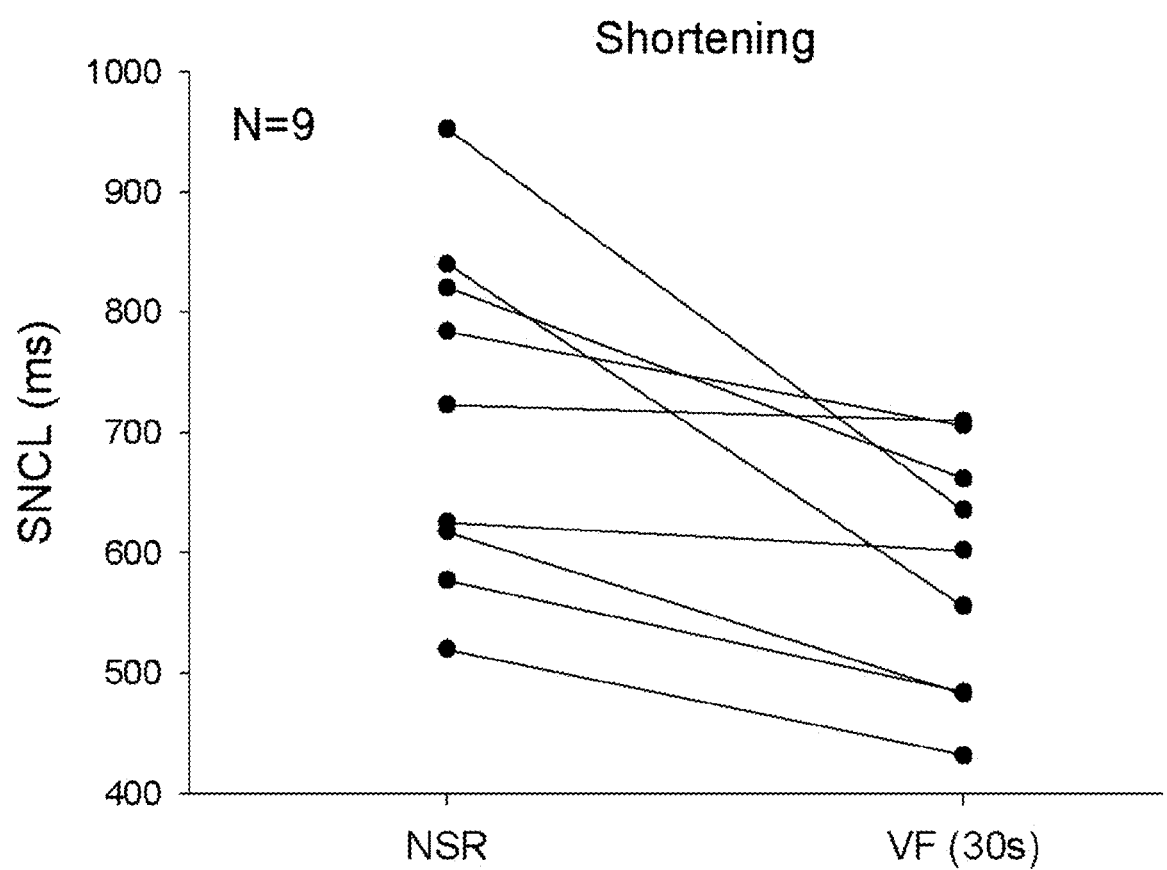
FIG. 10A depicts results of changing SNCL, compared to VF induction (NSR), and during a 30-second period of VF, in which the SNCL decreased.
Figure 10B:
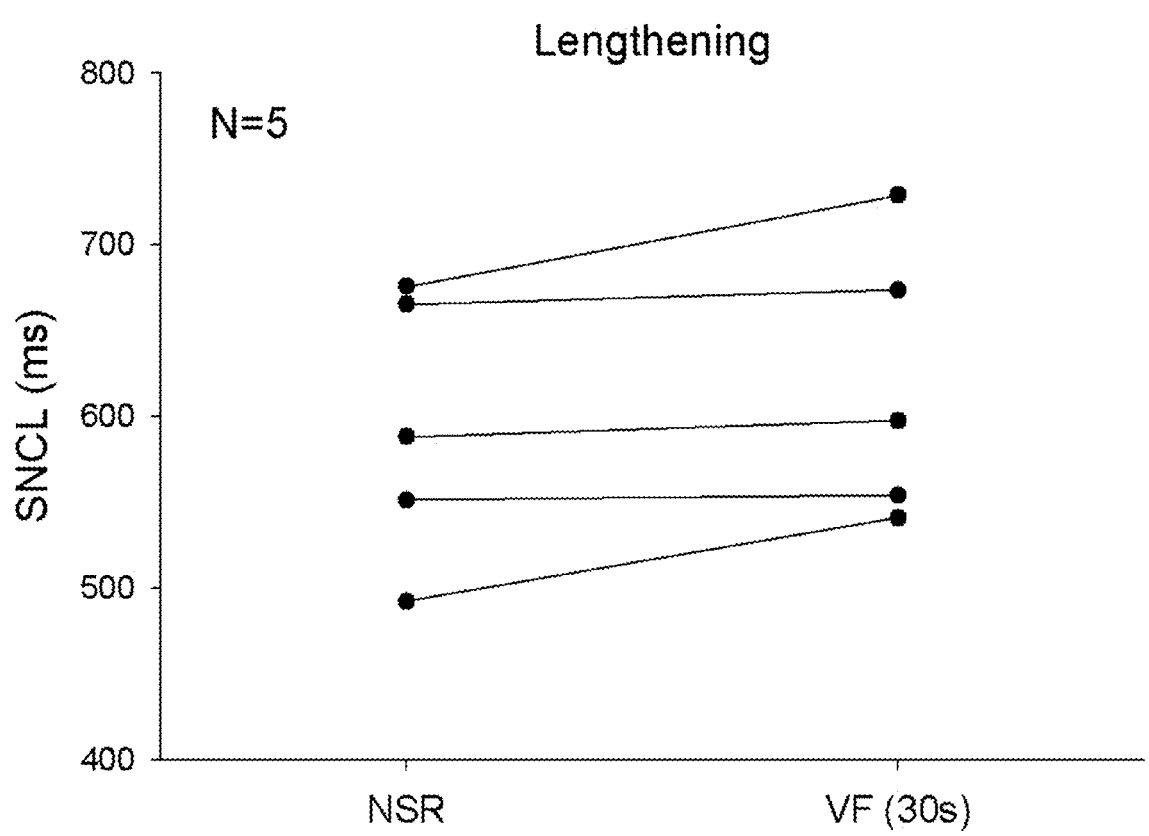
FIG. 10B depicts results of changing SNCL, compared to NSR, and during a 30-second period of VF, in which the SNCL increased.

While some studies have evaluated the autonomic changes prior to VF onset, the changes during VF remain poorly understood. Analysis of the SNCL changes during VF provides a unique opportunity to assess the autonomic changes. In fourteen anesthetized pigs, the chest was opened and the heart was exposed on a pericardial cradle. A 247-electrode sock was placed around the ventricles, an atrial lead over the right atrial appendage and an arterial catheter in the right femoral artery for blood pressure monitoring. Using DC current or the shock-on-T method, VF was induced and sustained for 30 seconds before applying DC shock. Mean SNCL was measured during the 10-second period prior to VF induction (NSR) and during the 30-second period of VF. Compared to NSR, SNCL during VF shortened in 9 animals and lengthened in 5 (36%), (see FIGS. 10A and 10B). As a group, the percent change in SNCL during the first 10-sec interval was greater than the percent change during the second and third 10-sec. intervals. Similarly, the percent change during the second 10-sec. interval was greater than the percent change in the third 10-sec interval. SNCL lengthening was observed in 36% of the pigs during the first 30 seconds of VF suggesting increased vagal tone or decreased sympathetic activity in one third of the cases. In addition, there was a gradual increase in SNCL regardless of the magnitude or direction of the initial change. The underlying mechanism of the SNCL changes and the clinical implications remain unknown.

The role of the baroreflex system in various tachyarrhythmias has been the subject of extensive research. During tachyarrhythmias, arterial blood pressure (BP) decreases while central venous pressure (CVP) increases. On one hand, the unloading of the arterial baroreceptors results in an increase in sympathetic nerve activity (SNA) and vagal inhibition via the arterial baroreflex. On the other hand, the increase in filling pressures results in a decrease in SNA and an increase in vagal tone via the cardiopulmonary baroreflex. These competing reflexes result in mixed messages to the central nervous system. It has been shown that during supraventricular and ventricular tachycardia, the arterial baroreflex predominates with minimal contribution from the cardiopulmonary reflex. Indeed, the net response during these tachycarrhythmias is a state of sympathoexcitation, which has been shown to correlate with blood pressure recovery. While the autonomic changes during supraventricular and ventricular tachycardia have been described, the responses during fast ventricular arrhythmias (FVA: VF and rapid VT with about CL<240 ms) remain unknown.

Assessment of the autonomic changes during ventricular arrhythmias is a challenge as the surface ECG prohibits the evaluation of sinus node function. Thus far, human studies have used microneurography as the only direct method for assessing the sympathetic changes during tachyarrhythmias. With the increased number of defibrillator implants incorporating atrial leads, analysis of the changes in sinus node cycle length (SNCL) from atrial electrograms recorded provides a unique opportunity to assess the autonomic changes that accompany these arrhythmias. We have recently shown in defibrillator patients that SNCL shortening during ventricular tachycardia, a marker of the degree of sympathoexcitation, was a predictor of successful anti-tachycardia pacing. Reflex sympathoexcitation is known to improve conduction and shorten ventricular refractory period, thus increasing the likelihood that a pacing impulse reaches the excitable gap and collides both orthodromically and antidromically with the tachycardia wavefront. In another study, we assessed whether the changes in SNCL during VF correlated with arterial baroreflex gain (BRG). BRG and SNCL measurements were successfully obtained in 18 patients undergoing the implantation of an implantable cardioverter defibrillator (ICD). During VF, SNCL shortened in 11 patients and surprisingly lengthened in 7 patients. We found no correlation between arterial BRG and percent change in SNCL. To our knowledge, the mechanisms underlying the SNCL changes during VF and VT with CL<240 ms remain unknown.

Determination of the mechanisms responsible for the SNCL changes during FVA (VF and VT with about CL<240 ms) and its relationship to peripheral sympathetic activity would be advantageous. It is believed the changes in SNCL during FVA are vagally mediated, and that the lengthening and shortening in SNCL are associated with a decrease and an increase in peripheral sympathetic activity respectively. Accordingly, it is understood that some patients develop paradoxically a vasovagal-like reaction during FVA, and the analysis of the SNCL could help identify this subgroup of patients.

Increased sympathetic activity during ventricular tachycardia has been shown to be beneficial. Indeed, our group has shown that the greater the sympathoexcitation was during ventricular tachycardia, the greater was the BP recovery both during and after tachycardia termination.

It is believed that the effects of FVA (VF and VT with about CL<240 ms) on peripheral sympathetic activity have not been evaluated. In addition, the role of the autonomic changes in mediating blood response and time to symptoms remain unknown. The study described above was the first to look at the sinus rate as a surrogate of the autonomic changes that occur during VF. If the lengthening and shortening in SNCL are indeed associated with a decrease and an increase in peripheral sympathetic activity respectively, then patients with SNCL lengthening should have a greater decrease in BP due to a decrease in arteriolar resistance, and earlier onset of symptoms when compared to patients with SNCL shortening. Conversely, patients with SNCL shortening would have a lesser decrease in BP due to elevated arteriolar resistance and delayed onset of symptoms when compared to patients with SNCL lengthening.

Determination of the role of the autonomic changes during FVA in predicting blood pressure response and time to symptoms would be advantageous. It is believed that the SNCL lengthening during FVA is associated with a greater decrease in blood pressure when compared to those with SNCL shortening. Furthermore, it is believed that patients with SNCL lengthening have a shorter time to near syncope and syncope when compared to those with SNCL shortening.

The number of implantable cardioverter-defibrillators (ICD) implants per year, at the time of this disclosure, about 50,000 and is expected to grow as an aging population and expanding ICD indications intersect. A sub-study of the MADIT II ICD recipients revealed that, over an average of 17.2 months of follow-up, 24% of ICD recipients received an appropriate ICD therapy. Some ICDs, have a variety of programmable options for antitachycardia pacing (ATP), which can be an effective alternative to shocks. Despite encouraging results from studies employing ATP algorithms, the clinical predictors of successful ATP remain poorly understood. Furthermore, this therapy is rarely used for the treatment of fast ventricular arrhythmias (CL<240 ms) because of the fear of syncope should ATP fails. Therefore, gaining an insight about the BP response and time to symptoms onset during FVA should greatly enhance our utilization of this painless therapy. Indeed, ICD shocks have shown to be associated with newly diagnosed depression and anxiety disorders in addition to their impact on battery life longevity. Therefore, any decrease in the number of shocks through the utilization of successful ATP should have a great impact on the quality of life of millions of Americans with ICD implants in addition to device longevity.

Information derived from the studies discussed above are incorporated into an algorithm that uses ATP therapy in patients with FVA. As stated above, ATP is rarely used for the treatment of FVA (CL<240 ms) because of the fear of syncope should ATP fails. It is believed that the SNCL changes can provide further information on the early BP response and time to symptoms in patients with FVA. In specific, it is believed that anti-tachycardia pacing reduces shock therapy for fast ventricular arrhythmias in patients with SNCL shortening without a significant increase in acceleration or syncope.

Supraventricular tachycardias (SVT) with a 1:1 atrioventricular (AV) relationship are classified according to the location of the P wave in relation to the QRS: Short RP tachycardias (RP<PR), long RP (RP>PR) tachycardias and tachycardias with no identifiable P waves. Little is known about the significance of the P wave relation to the QRS in terms of hemodynamic and neural outcome. The effect of atrial systole timing on the hemodynamic and sympathetic neural response during rapid dual chamber pacing (DDD) was evaluated in 10 patients with a DDD pacemaker. Blood pressure, central venous pressure and sympathetic nerve activity (SNA) were recorded continuously during rapid DDD pacing at a rate of 175 bpm (CL=342 ms) with 3 AV intervals: AV=30 ms, AV=200 ms and AV=110 ms, simulating SVT with no identifiable P wave, short RP and long RP tachycardia respectively. The relationship of atrial systole to ventricular systole was found to play a major role in the hemodynamic and neural response during tachycardia, with long RP tachycardia having the most favorable response. The changes in SNA seem to parallel the changes in mean BP with no clear evidence of predominant atrial vasodepressor response.

Figure 2A:
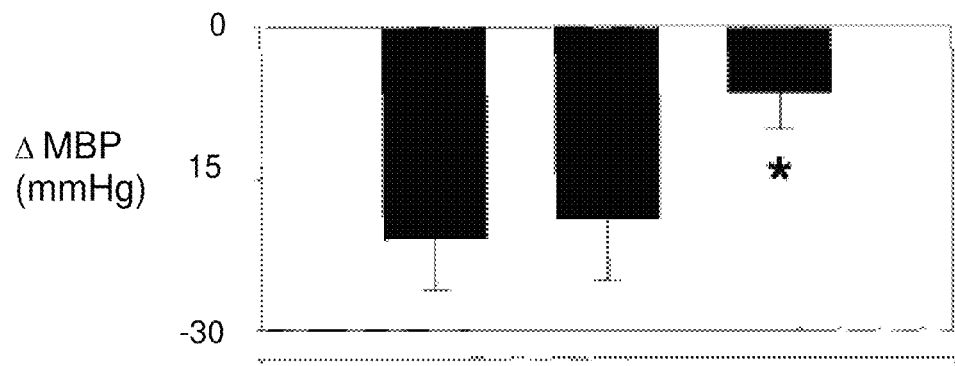
FIG. 2A depicts changes in mean blood (arterial) pressure (MBP, MAP) during pacing, in accordance with embodiments described herein, with near simultaneous atrial and ventricular systole (A&V), short-RP tachycardia, and long-RP tachycardia.
Figure 2B:
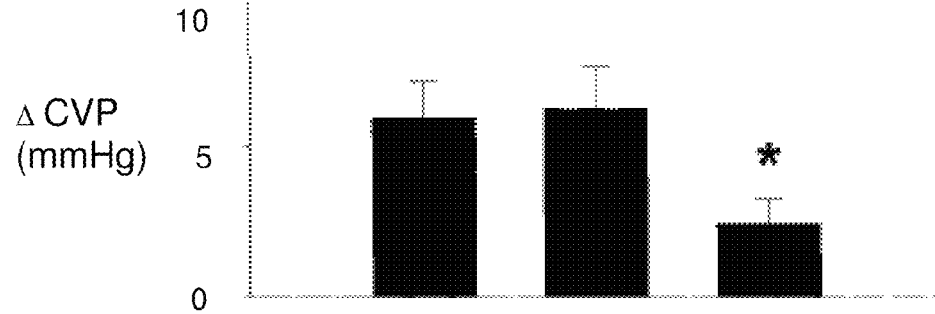
FIG. 2B depicts changes in central venous pressure (CVP) during pacing, in accordance with embodiments described herein, with near simultaneous atrial and ventricular systole (A&V), short-RP tachycardia, and long-RP tachycardia.
Figure 2C:
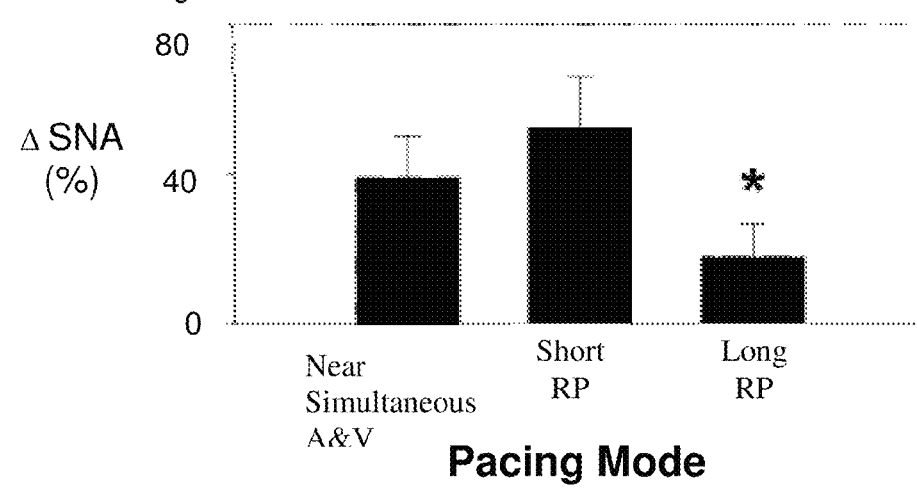
FIG. 2C depicts changes in sympathetic nerve activity (SNA) during pacing, in accordance with embodiments described herein, with near simultaneous atrial and ventricular systole (A&V), short-RP tachycardia, and long-RP tachycardia.
Figure 3A:
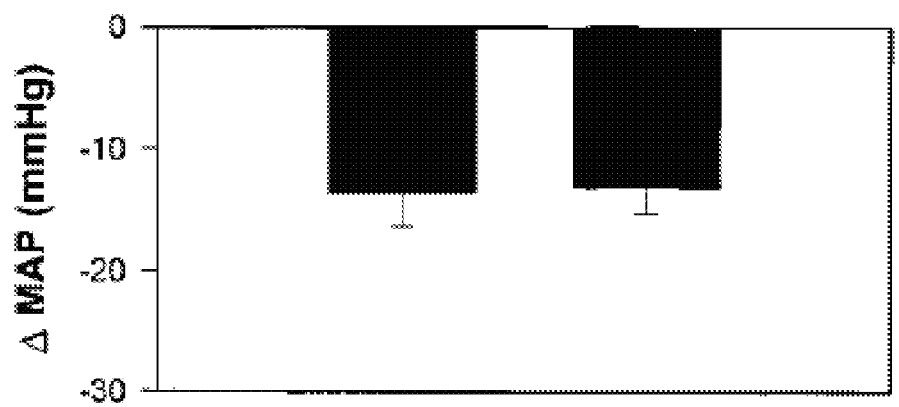
FIG. 3A depicts changes in MAP in response to pacing and nitroprusside infusion (NTP).
Figure 3B:
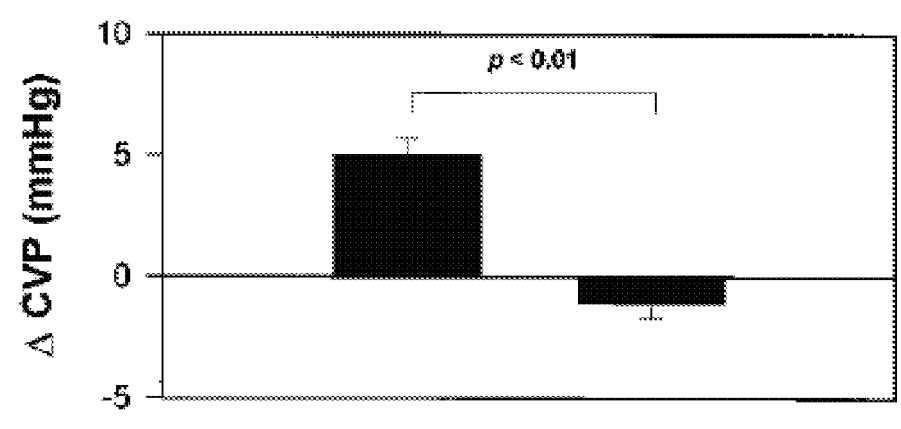
FIG. 3B depicts changes in CVP in response to pacing and nitroprusside infusion (NTP).
Figure 3C:
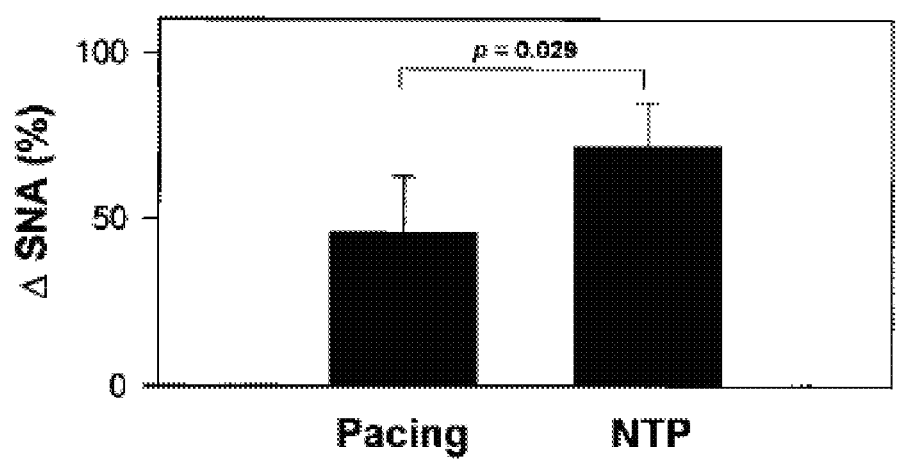
FIG. 3C depicts changes in SNA in response to pacing and nitroprusside infusion (NTP).
Figure 4:
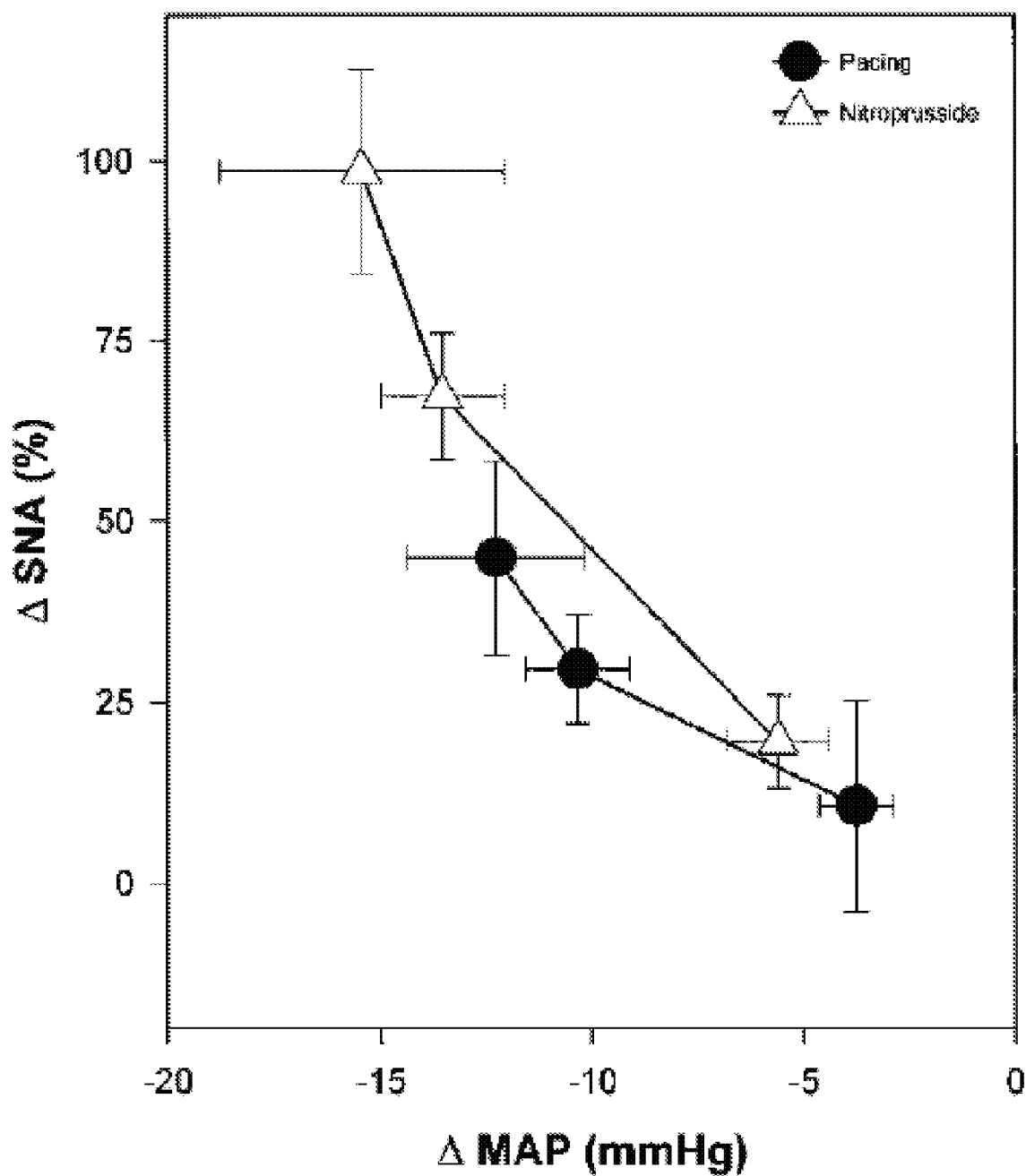
FIG. 4 depicts a chart comparing changes in MAP and SNA in response to pacing and nitroprusside infusion (NTP).

FIG. 1 depicts sample tracings of integrated sympathetic neurogram, arterial BP, CVP, and ECG during baseline (prepacing) and during minute 3 of rapid pacing (175 bpm) with either near-simultaneous atrial and ventricular systole (A&V), short-RP tachycardia, or long-RP tachycardia. In this individual, it is apparent that long-RP tachycardia produced a higher arterial BP, lower CVP, and less increase in SNA. FIGS. 2A-2C depict changes (mean±SEM) in MAP (DMAP), CVP (DCVP), and SNA (DSNA) during minute 3 of pacing with near simultaneous atrial and ventricular systole (A&V), short-RP tachycardia, and long-RP tachycardia. The asterisks * in FIGS. 2A-2C indicate a significant difference from the other 2 pacing modes (P<0.05).

During ventricular tachycardia, BP decreases while CVP increases. The decrease in BP is expected to result in an increase in SNA due to unloading of the arterial baroreceptors, while the increase in CVP should result in a decrease in SNA due to activation of the cardiopulmonary baroreceptors. It is believed that arterial BRG predominated in mediating the sympathetic changes with minimal contribution from the cardiopulmonary baroreceptors. Furthermore, it is believed that arterial BRG correlated with the hemodynamic outcome during sustained ventricular tachycardia. In a test, efferent postganglionic muscle SNA, BP and CVP were measured during ventricular pacing (3 pacing CLs) and compared to the responses to 3 doses of nitroprusside infusion (NTP). We also measured SNA, BP and CVP during VP (400 ms) under 3 conditions: 1) Pacing alone, 2) Pacing+Head-up tilt, and 3) Pacing+Phenylephrine. FIGS. 3A-3C and FIG. 4 depict mean±SEM responses to pacing and NTP that produced comparable decreases in MAP (13.6±2.7 vs 13.2±1.8 mmHg).

Figure 5A:
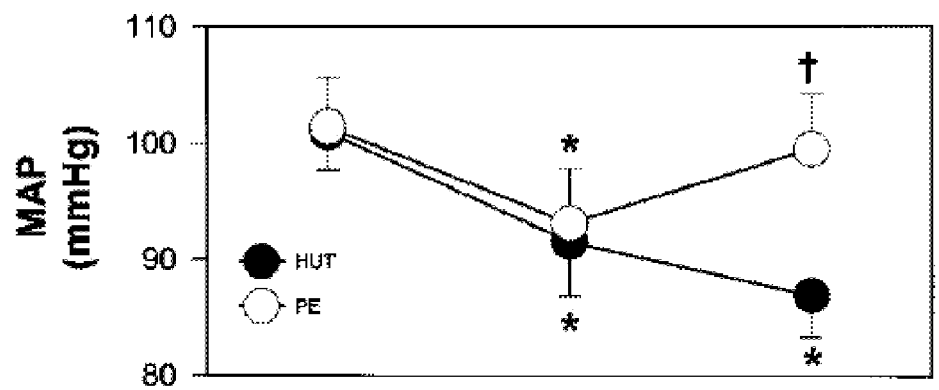
FIG. 5A depicts changes in MAP in response to ventricular pacing (VP) and VP with phenylephrine infusion (PE) or head-up tilt (HUT).
Figure 5B:
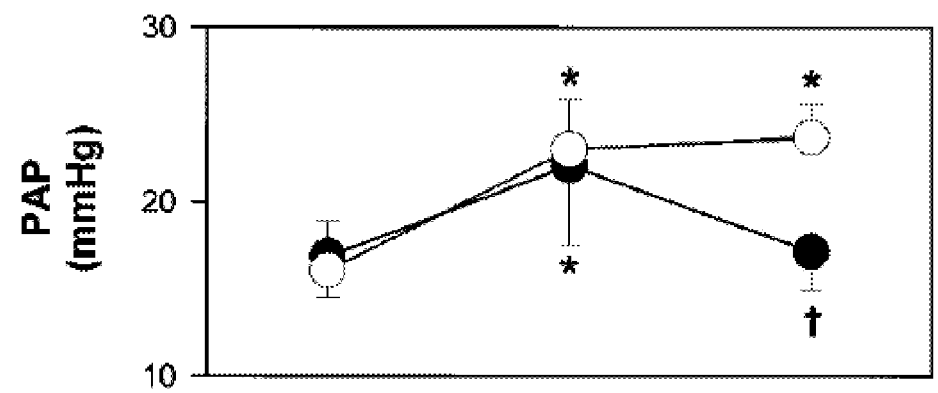
FIG. 5B depicts changes in pulmonary arterial pressure (PAP) in response to ventricular pacing (VP) and VP with phenylephrine infusion (PE) or head-up tilt (HUT).
Figure 5C:
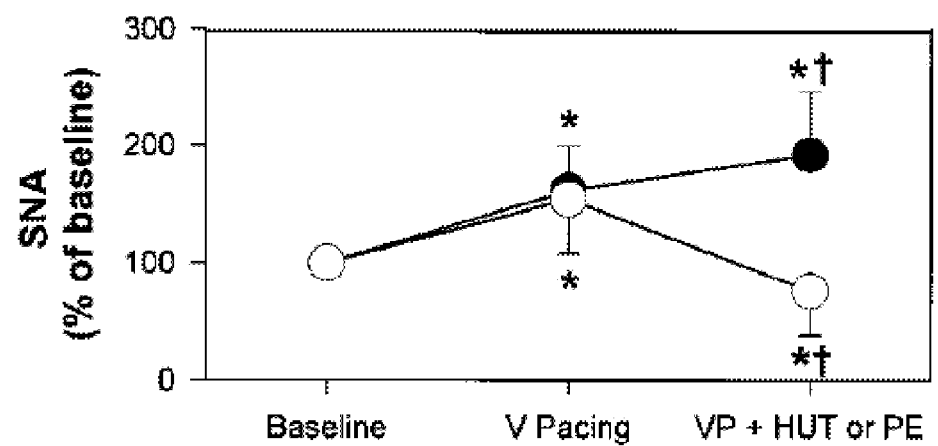
FIG. 5C depicts changes in SNA in response to ventricular pacing (VP) and VP with phenylephrine infusion (PE) or head-up tilt (HUT).

NTP resulted in a significantly greater increase in SNA when compared to VP (FIGS. 3A-3C and 4). The reason for that is that while both NTP and VP resulted in a decrease in BP and thus unloading of the arterial baroreceptors, NTP infusion was associated with a decreased in CVP while VP resulted in an increase in CVP. A decrease in CVP results in a greater increase in SNA due to unloading of the cardiopulmonary baroreceptors. On the other hand, an increase in CVP results in sympathoinhibition due to activation of the cardiopulmonary baroreceptors. The fact that VP resulted in an increase in SNA despite the increase in CVP suggests that arterial BRG predominates in mediating the SNA changes with minimal contribution form the cardiopulmonary BRG. This point is further illustrated in FIGS. 5A-5C where head-up tilt added to VP resulted in a greater increase in SNA due to the associated reduction in CVP. On the other hand, phenylephrine infusion resulted in a decrease in SNA due to the increase in BP, which was the main trigger for the increase in SNA. FIGS. 5A-5C depict summary data for MAP, PAP and SNA responses to ventricular pacing (VP) and VP with phenylephrine infusion (PE, ○) or head-up tilt (HUT, ).

Mean±SEM. The * indicates a significant difference from baseline (p<0.05), and the † indicates a significant difference from VP alone.

Figure 6:
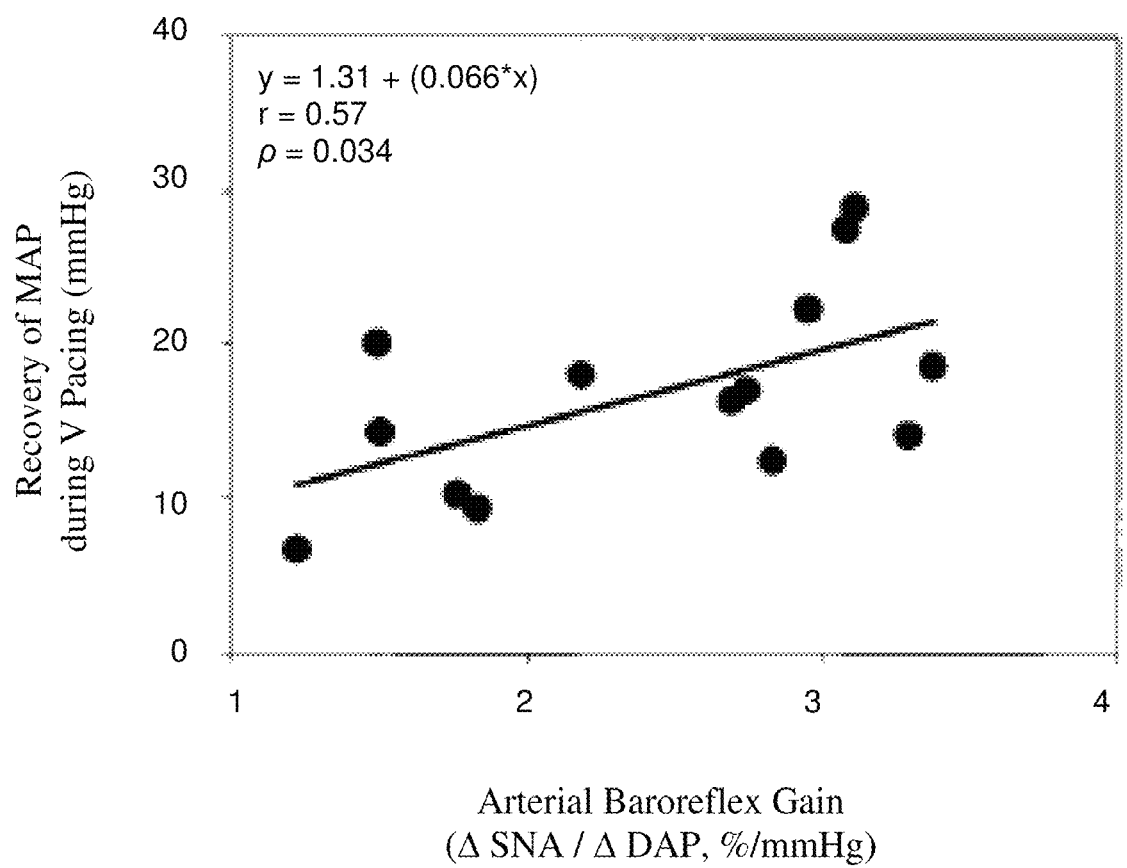
FIG. 6 depicts a relationship of recovery of MAP during VP to arterial baroreflex sympathetic gain estimated during NTP infusion.

To test the proposal that arterial BRG was a predictor of hemodynamic outcome during VT, sympathetic nerve activity (SNA), BP and central venous pressure were measured in 14 patients during nitroprusside (NTP) infusion and during rapid VP, simulating VT. Arterial BRG was defined as the slope of the relationship of change in SNA (%) to change in diastolic BP during NTP. BP recovery during sustained VP was defined as the change in BP from the nadir to steady state during sustained pacing. We found that arterial BRG correlated positively with mean BP recovery (r=0.57) (See FIG. 6). FIG. 6 depicts the relationship of recovery of MAP during VP to arterial baroreflex sympathetic gain estimated during NTP infusion. Recovery of MAP was determined as a change in MAP from nadir at onset of pacing to steady-state level after 1 minute of pacing. Recovery of MAP correlated positively with arterial baroreflex gain (r=0.57, P=0.034) and diastolic arterial pressure is references as DAP.

While the above 2 studies evaluated the SNA changes during simulated SVT and VT, the SNA response during VF and rapid VT with CL<240 ms, remain unknown.

Analysis of the changes in sinus node cycle length (SNCL) during VF inductions in patients undergoing the implantation of a defibrillator incorporating an atrial lead provides a unique opportunity to assess the autonomic changes that accompany VF. The purpose of this study was to assess whether the arterial baroreflex, as measured by arterial baroreflex gain (BRG), was a predictor of the change in SNCL during VF and of BP recovery following successful defibrillation. We believed that SNCL changes during VF would correlate with arterial BRG, i.e., the greater the arterial BRG is, the greater the shortening in SNCL during VF. Arterial BRG was measured using the modified Oxford technique in 18 patients referred for the implantation of a defibrillator incorporating an atrial lead. The average SNCL was measured during the 5 seconds prior to VF induction and the last 5 seconds during VF before defibrillation. Percent SNCL change (%ΔSNCL) was determined.

Arterial BRG ranged between −3 and 18 ms/mmHg. During VF, SNCL shortened in 11 patients (Group A, mean %ΔSNCL=−15%), and surprisingly lengthened in 7 patients (Group B, mean %ΔSNCL=5%). There was no correlation between %ΔSNCL and arterial BRG gain (r=0.25, p=0.32). In fact, arterial BRG in Group A was lower when compared to Group B (p=0.075). Sample tracings showing SNCL shortening and lengthening during VF are provided in FIGS. 7 and 8A-8B.

Figure 7:
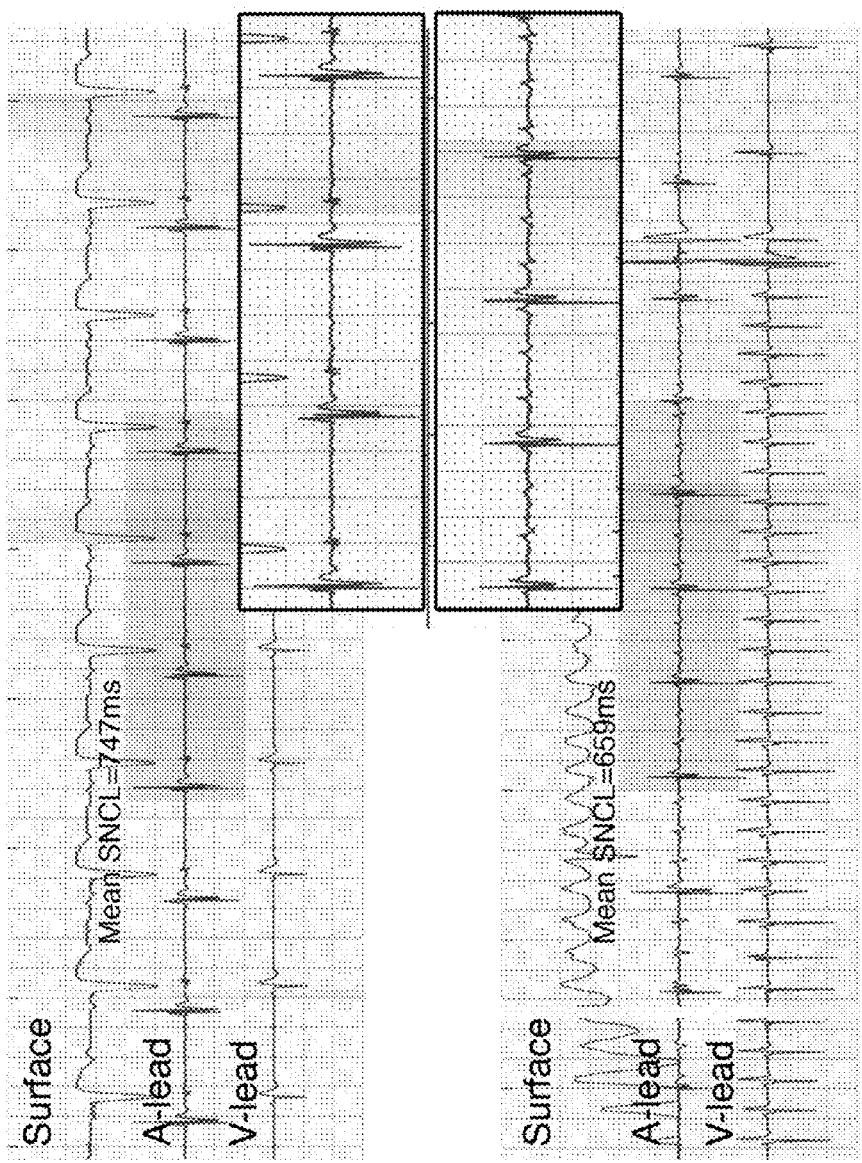
FIG. 7 depicts an upper depicting normal sinus rhythm with a sinus node cycle length (SNCL) equal to about 747 ms and a lower panel during VF, the mean SNCL decreased to 659 ms.

FIG. 7 depicts, in the upper panel, the normal sinus rhythm with a SNCL equal 747 ms. In the lower panel, FIG. 7 depicts, during VF, the mean SNCL decreased to 659 ms. For each panel, from top to bottom; surface ECG, atrial (A) signal, ventricular (V) signal, timing markers are illustrated, and the highlighted segment of the atrial signals are enlarged.

Figure 8A:
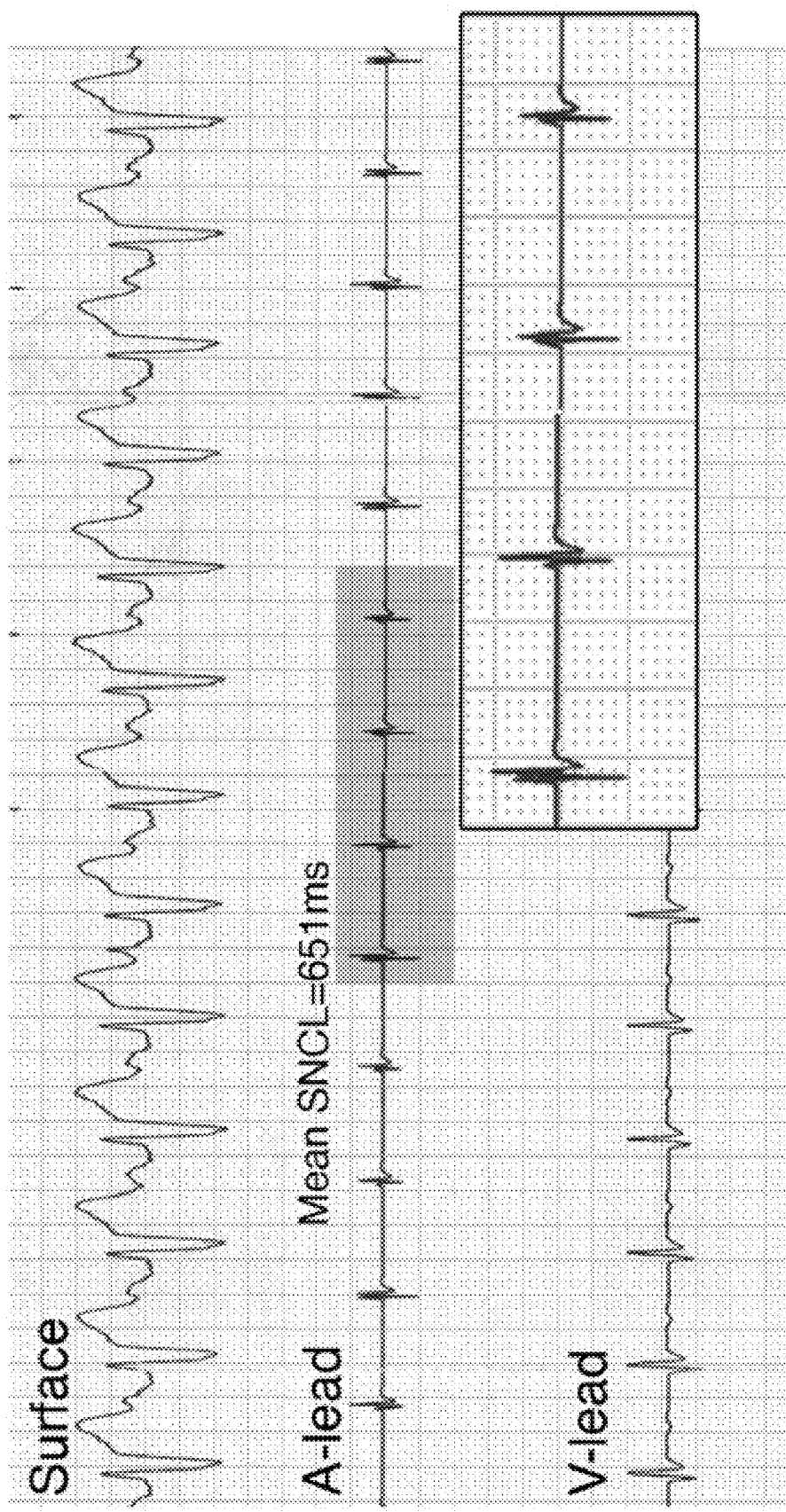
FIG. 8A depicts a normal sinus rhythm with a mean SNCL equal to about 651 ms.
Figure 8B:
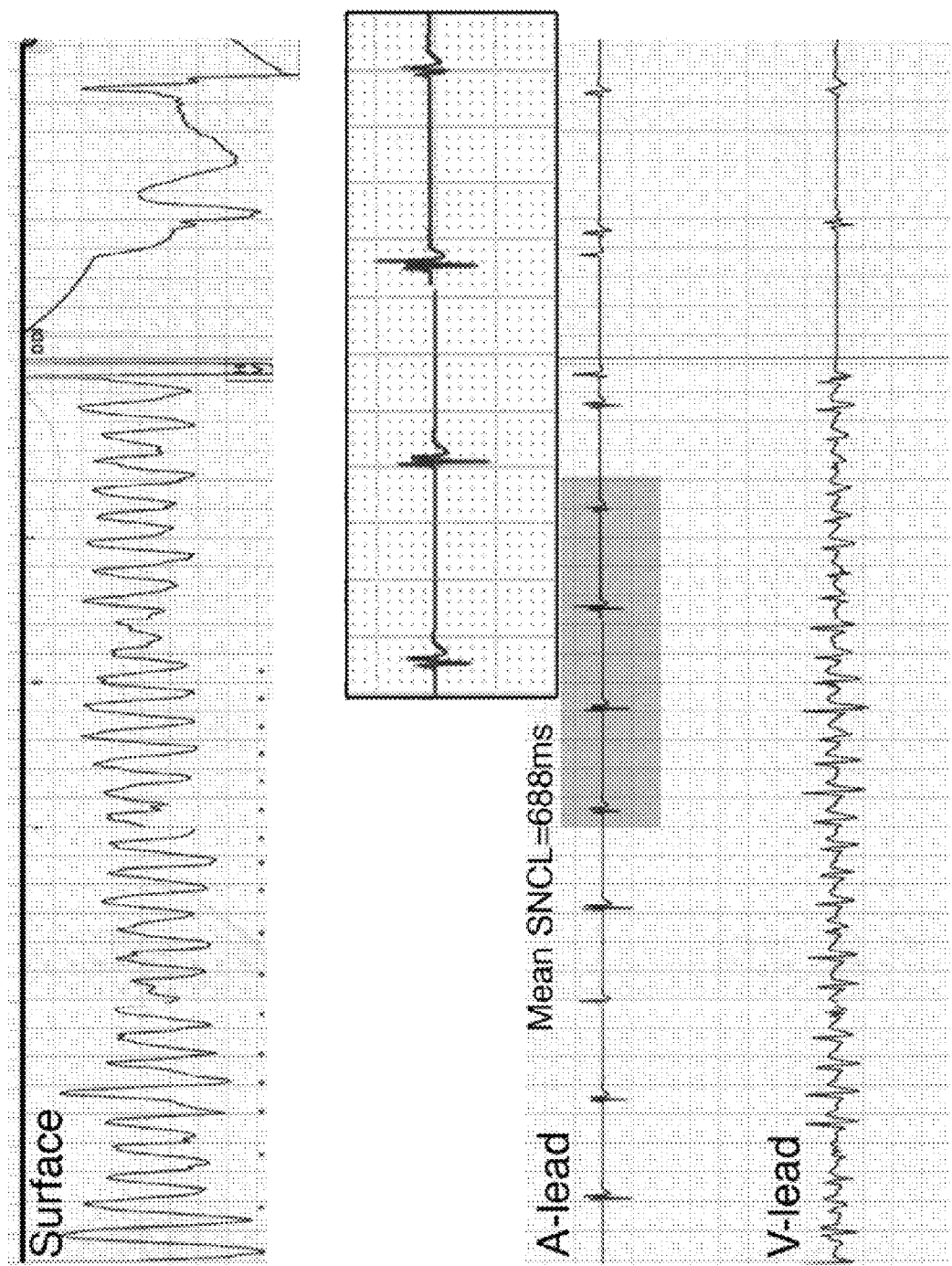
FIG. 8B depicts, during VF, the mean SNCL having increased to about 688 ms.

FIG. 8A depicts the normal sinus rhythm with a mean SNCL equal to 651 ms. FIG. 8B depicts, during VF, the mean SNCL did not decrease but rather increased to 688 ms. For each figure, from top to bottom, surface ECG, timing markers, atrial (A) signal, ventricular (V) signal are provided. The highlighted segments of the atrial signals are enlarged.

This recent study highlights a significant new finding: SNCL lengthening during VF in almost 40% of the patients. The mechanisms underlying the SNCL changes and the clinical implications are unknown. Furthermore, whether the same findings occur with rapid VT with CL<240 ms remain unclear.

It is believed that, with respect to the mechanisms of SNCL changes during FVA, changes in SNCL during FVA are vagally mediated. A test was conducted in a swine model where SNCL changes will be measured during VF and RVP before and after selective parasympathetic, sympathetic and complete autonomic blockade.

Figure 9:
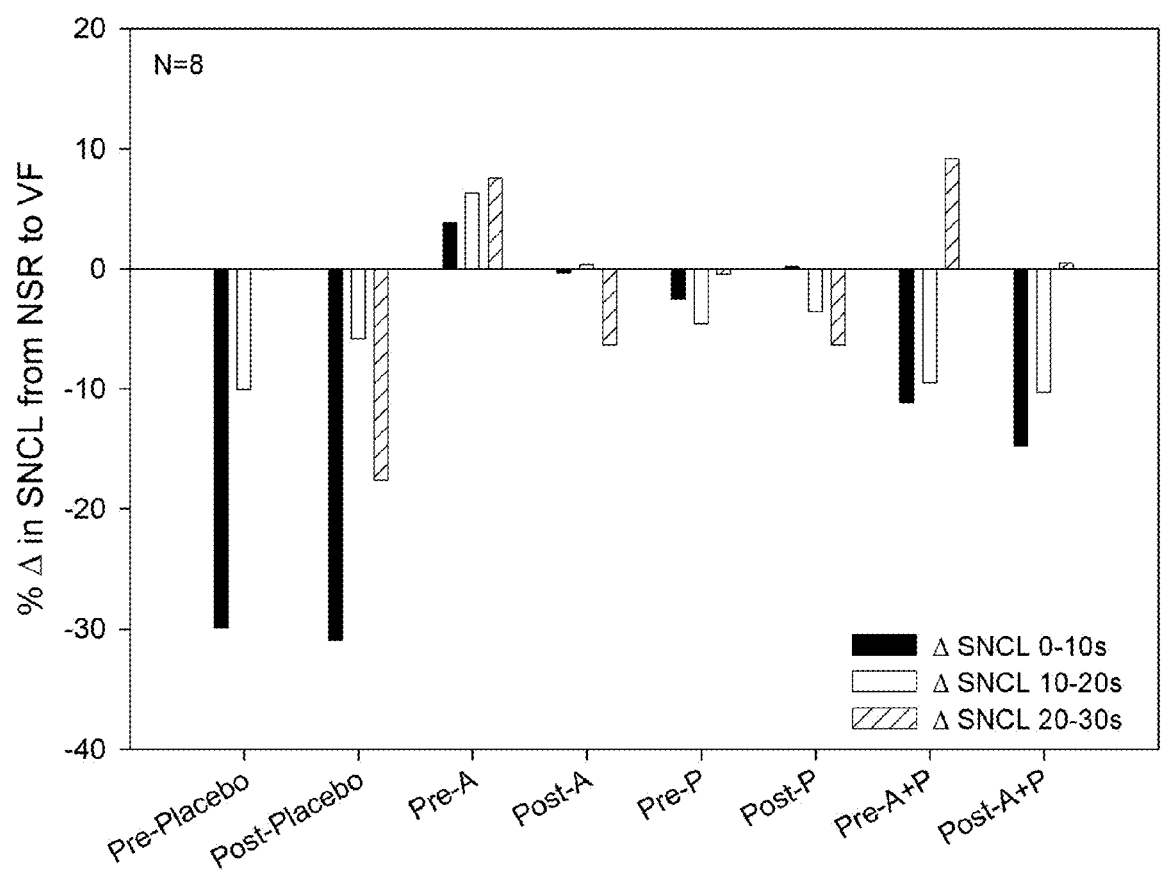
FIG. 9 depicts the percent change in SNCL from baseline at baseline and following the administration of placebo, atropine (A), propranolol (P) and atropine in addition to propranolol (A+P).

In 8 anesthetized pigs, the chest was opened and the heart was exposed on a pericardial cradle. An atrial lead was placed over the right atrial appendage and an arterial catheter in the right femoral artery for BP monitoring. Using DC current or the shock-on-T method, VF was induced and sustained for 30 seconds before applying a DC shock. Following a 10 minute recovery period, atropine (A, n=2) at 0.04 mg/kg, propranolol (P, n=2) at 0.2 mg/kg, both (A+P, n=2) or neither (Placebo, n=2) were administered at random, and VF was re-induced. SNCL changes were assessed before and after drug/placebo administration. Percent SNCL change (%ΔSNCL) was defined as %ΔSNCL=(VF-SNCL−Baseline-SNCL)/(Baseline-SNCL)*100. Atropine administration reversed the SNCL lengthening observed in the 2 pigs while propranolol had no effect on SNCL shortening observed in the 2 other pigs. FIG. 9 depicts the %ΔSNCL at baseline and following the administration of placebo, atropine (A), propranolol (P) and atropine in addition to propranolol (A+P). Our findings suggest that the SNCL changes during the first 30 seconds of VF appear to be vagally mediated.

While the study above is assessing the mechanism of SNCL changes during FVA, the relationship between these changes and peripheral sympathetic activity remain unknown. It is believed that the lengthening and shortening in SNCL are associated with a decrease and an increase in peripheral sympathetic activity respectively. A test was conducted in patients undergoing the implantation of dual chamber ICDs or a generator change. Using the microneurography technique described above, muscle SNA and the SNCL changes during VF inductions and RVP were recorded.

Patients receiving dual chamber ICD implants with defibrillation threshold testing were asked to enroll. SNA recordings were attempted in all patients. In addition, the mean SNCL was measured during the 5 seconds preceding VF onset and the last 5 seconds before defibrillation. Successful SNA recordings were obtained in 3 patients. Sympathoinhibition was observed during VF in 2 patients while sympathoexcitation was noted in the remaining patient. FIGS. 11A-11C show a muscle SNA recording from one of the patients who developed sympathoinhibition during VF. Almost complete sympathetic shut down was noted when compared to baseline. SNCL did not change and even lengthened by 3% in the patient with sympathoinhibition whereas it shortened by 13% in the patient with sympathoexcitation. Our findings of sympathoinhibition associated with SNCL lengthening suggest the presence of vasovagal like physiology during VF in a subgroup of patients.

Figure 12:
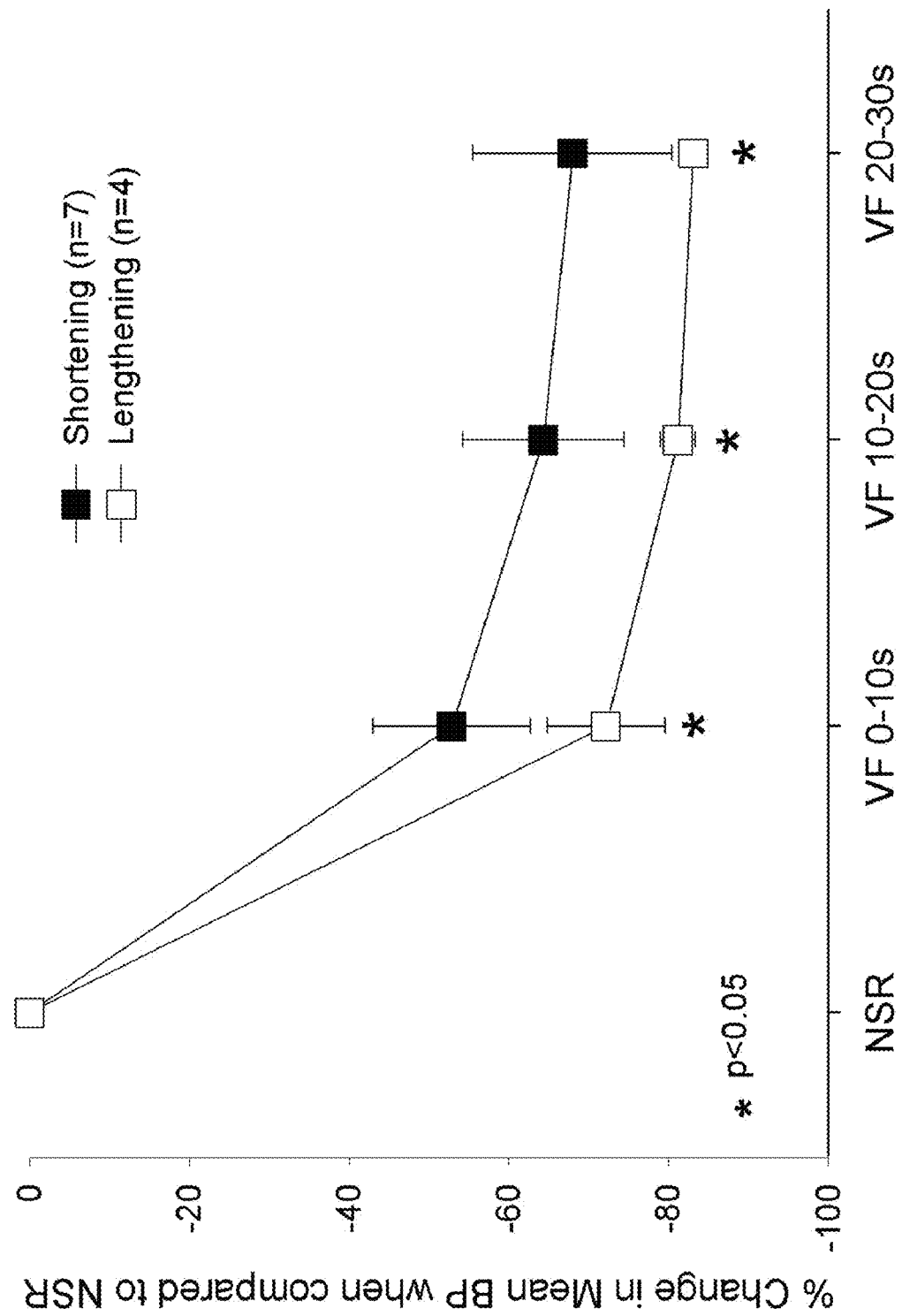
FIG. 12 depicts changes in MBP when compared to NSR during 10-second increments of a 30-second period of VF.

We also sought to determine the role of the autonomic changes during FVA in predicting blood pressure response and time to symptoms' onset. A test was conducted to determine that SNCL lengthening during FVA is associated with a greater decrease in blood pressure when compared to those with SNCL shortening. In 11 anesthetized pigs, the chest was opened and the heart was exposed on a pericardial cradle. A 247-electrode sock was placed around the ventricles, an atrial lead over the right atrial appendage and an arterial catheter in the right femoral artery for blood pressure monitoring. Using DC current or the shock-on-T method, VF was induced and sustained for 30 sec. before applying a DC shock. Animals were divided in to 2 groups based on SNCL response during VF: Shortening group (n=7, %ΔSNCL=−17%), Lengthening group (n=4, %ΔSNCL=4%). In the Shortening group, mean BP fell by 53% in the first 10 sec. when compared to NSR and continued to fall to 64% and 68% at 20 sec. and 30 sec. respectively. In the Lengthening group, BP fell by 72%, 81% and 83% when compared to baseline. The differences in percent decrease in BP between the groups were statistically significant at all 3 time points during VF ($p<0.05$). SNCL lengthening was associated with a greater decrease in BP when compared to SNCL shortening. The above findings suggest that SNCL changes during VF might be helpful in predicting the magnitude of the hemodynamic fall in BP. Such information could be useful in deciding who has "time" for painless therapy before delivering shock therapy in patients with dual chamber ICDs. SNCL lengthening was associated with a greater decrease in BP when compared to SNCL shortening. FIG. 12 depicts changes in MBP when compared to NSR during 10-second increments of a 30-second period of AF.

Figure 13:
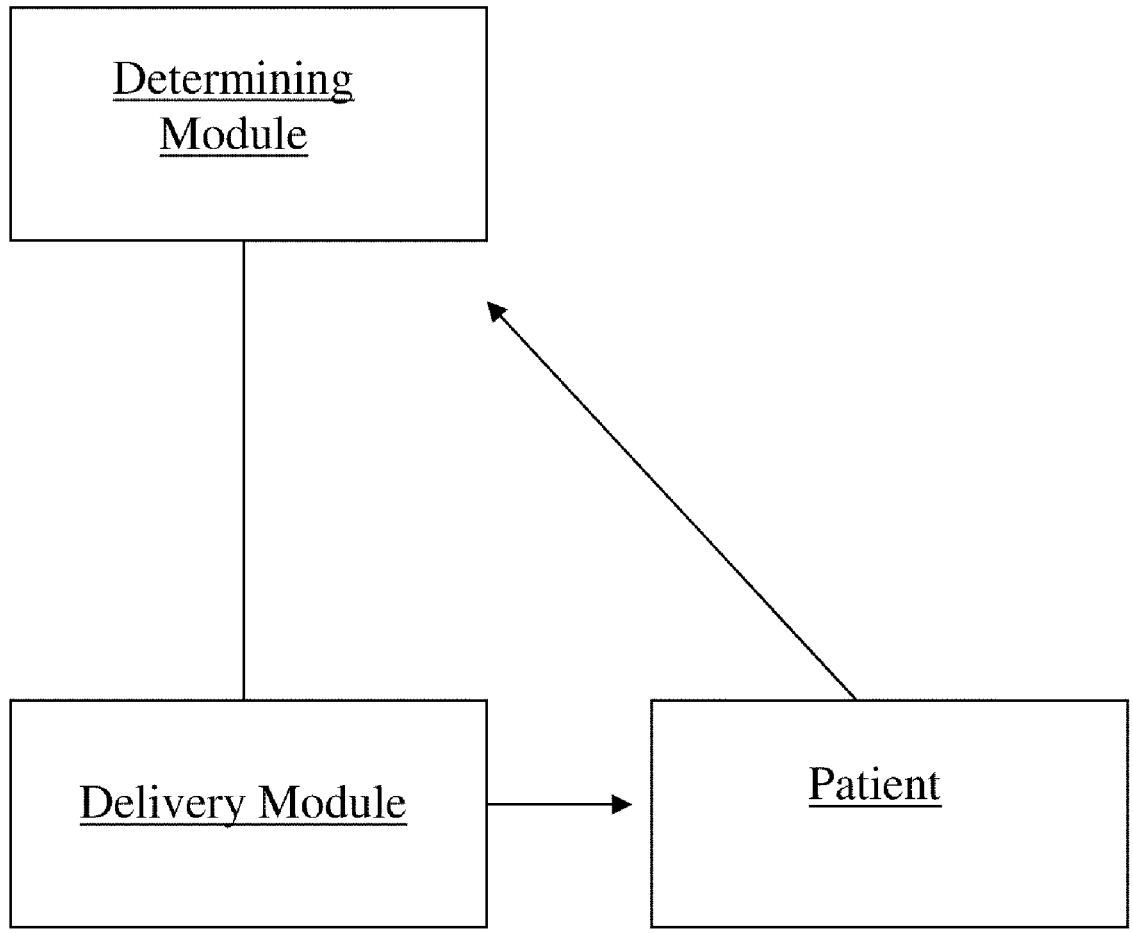
FIG. 13 depicts a determining module in connection with a delivery module, in accordance with embodiments described herein.

FIG. 13 depicts a determining module that can, for, example, determine a value of a parameter indicative of a rate of an intrinsic pacemaker of a heart of a patient experiencing a FVA. Also depicted is a delivery module, programmed to deliver a first therapy, for terminating the FVA, to the patient if the value indicates the depolarization rate is about equal to or higher than a threshold, and to deliver a second therapy, for terminating the FVA, different from the first therapy, to the patient if the value indicates the depolarization rate is lower than the threshold. In some embodiments, the determining module receives information from the patient, as indicated in FIG. 13. FIG. 13 also shows delivery of therapy from the delivery module to the patient.

Figure 14:
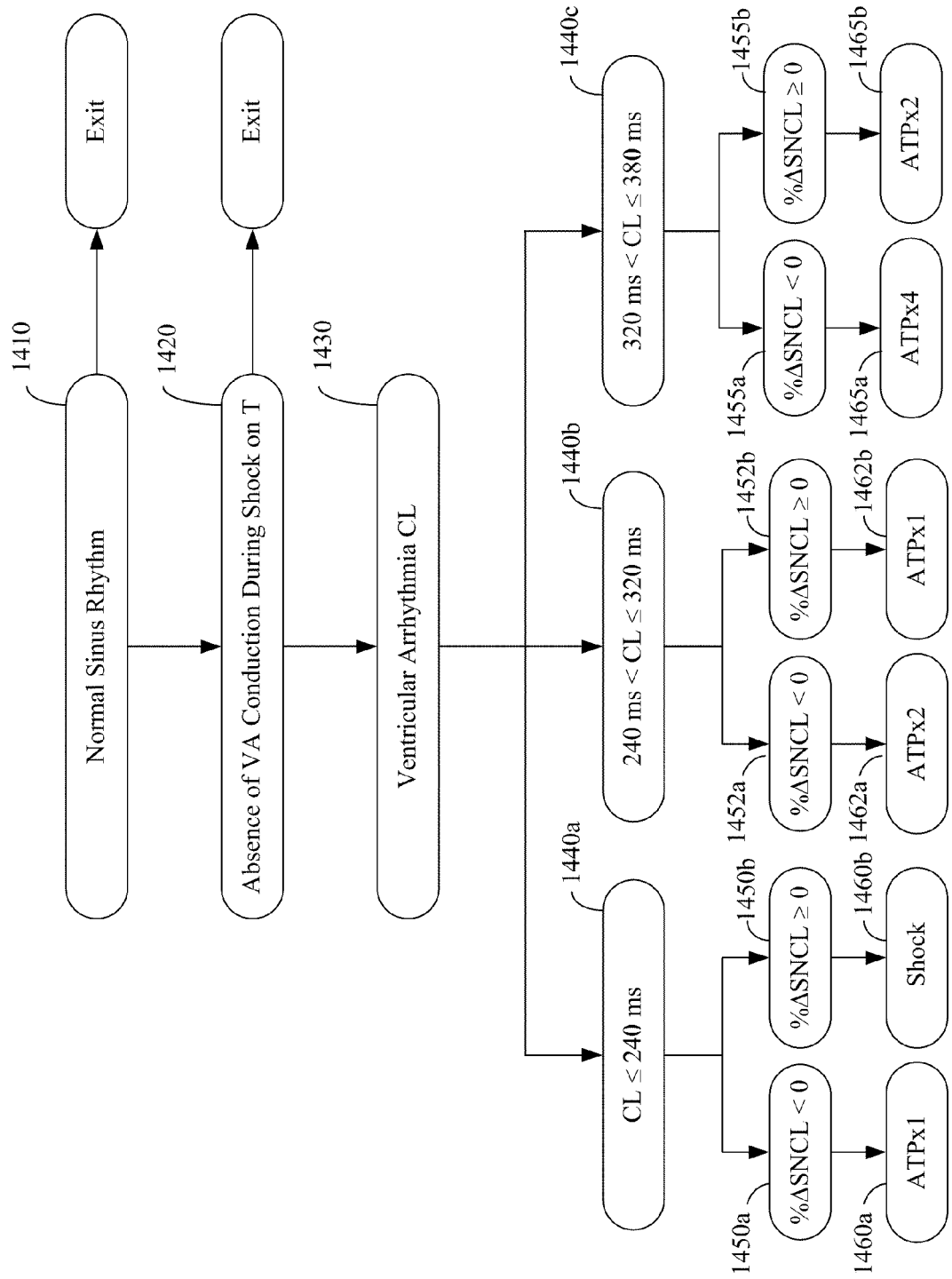
FIG. 14 is a flowchart of a method for treating ventricular arrhythmia according to an embodiment of the present invention

FIG. 14 is a flowchart of a method for treating an abnormal heart rhythm, such as ventricular arrhythmia. The method may be used to determine when it is appropriate to treat the abnormal heart rhythm, such as ventricular arrhythmia, with painless therapy, such as ATP, instead of shock therapy. As discussed above, while shock therapy is effective at terminating ventricular arrhythmia, shock therapy involves the delivery of painful shocks to the patient, which negatively impacts the quality of life of the patient. In addition, shock therapy may lead to myocardial damage and quickly drain the battery of an ICD. Thus, it can be desirable to treat ventricular arrhythmia with painless therapy in cases where the painless therapy will be effective to avoid subjecting the patient to painful shocks. However, if the painless therapy fails, the patient may lose consciousness. In addition, the failed treatment attempt delays the use of shock therapy. The delay may decrease the success rate of subsequent shocks.

In one embodiment, the method determines a change in the sinus node cycle length (SNCL) of the patient's heart between a time prior to the onset of ventricular arrhythmia and a time during the ventricular arrhythmia. It is believed that SNCL lengthening during ventricular arrhythmia correlates with a more rapid drop in blood pressure and a shorter time to syncope compared to SNCL shortening. As a result, for a patient with SNCL lengthening during ventricular arrhythmia, there be may less time to attempt painless therapy before syncope and a lower likelihood of success of painless therapy. Thus, the method may use the change in SNCL to predict the likelihood of success of painless therapy and to determine whether to use painless therapy to treat a particular episode of ventricular arrhythmia, as discussed further below.

A method for treating ventricular arrhythmia according to various embodiments will now be described with reference to FIG. 14. The method may include determining a change in the SNCL of a heart of a patient between a time prior to an abnormal heart rhythm and a time during the abnormal heart rhythm, and determining which one of a plurality of different therapies to deliver to the patient to treat the abnormal heart rhythm based on the change in the SNCL.

In step 1410, the method determines whether the heart has a normal sinus rhythm. This may be determined by sensing electrical activity of the heart using one or more implanted electrodes. If the heart has a normal sinus rhythm, then the method proceeds to step 1420. Otherwise, the method is exited.

In step 1420, the method determines whether Ventriculoatrial (VA) conduction is absent during the induction of VF using the shock on T method. VA conduction may occur when electrical signals propagate from the ventricle to the upper chambers of the heart. These electrical signals may result in electrical noise in the upper chambers of the heart that prevents an accurate determination of the sinus node cycle length. The shock on T may be used to artificially induce an abnormal heart rhythm when an ICD is first implanted in the patient to test whether the ICD is functional. If VA conduction is absent during the shock on T, then the method proceeds to step 1430. Otherwise the method is exited. After implantation of the IDC, step 1420 may be omitted.

In step 1430, the method determines whether the heart is experiencing a ventricular arrhythmia. This may be done by measuring a rate of electrical impulses in the ventricle using one or more implanted electrodes and detecting the ventricular arrhythmia when the rate exceeds a threshold. Other methods known in the art may also be used to detect ventricular arrhythmias. The method also determines the cycle length of the ventricular arrhythmia. This may be done by measuring the time between consecutive impulses in a ventricle or other method.

The method then proceeds to one of steps 1440a-1440c depending on the cycle length of the ventricular arrhythmia. When the cycle length is less than about 240 ms, corresponding to rapid ventricular arrhythmia, the method proceeds to step 1440a. When the cycle length is between about 320 ms and about 240 ms, the method proceeds to step 1440b. Finally, when the cycle length is between about 380 ms and about 320 ms, the method proceeds to step 1440c. The cycle length ranges in FIG. 14 are exemplary only and other cycle length ranges may be used.

In step 1440a, the method determines a change in the SNCL between a time prior to the onset of the ventricular arrhythmia and a time during the ventricular arrhythmia. In one embodiment, the change in the SNCL may be given as a percent SNCL change (%ΔSNCL). The percent SNCL change may be defined as %ΔSNCL=(VA−SNCL−Baseline−SNCL)/(Baseline−SNCL)*100, where VA−SNCL is the SNCL during the ventricular arrhythmia and Baseline−SNCL is the SNCL prior to the onset of the ventricular arrhythmia. The VA−SNCL may be obtained by computing the mean SNCL during a time window (e.g., 10 seconds or less) after the onset of the ventricular arrhythmia. The Baseline−SNCL may be obtained by computing the mean SNCL during a time window (e.g., 60 seconds or less) prior to the onset of the ventricular arrhythmia. The SNCL may be determined by measuring the time between consecutive electrical impulses in the upper chambers of the heart using one or more implanted electrodes.

When %ΔSNCL is less than zero, the method proceeds to step 1450a. This occurs when the SNCL shortens during ventricular arrhythmia compared to the time prior to the ventricular arrhythmia. In this case, the method delivers ATP to the patient to treat the ventricular arrhythmia in step 1460a.

The ATP may comprise a sequence of pulses delivered to one or both ventricles of the heart using one or more implanted electrodes.

When %ΔSNCL is equal to or greater than zero, the method proceeds to step 1450*b*. This occurs when the SNCL does not change or lengthens during ventricular arrhythmia compared to the time prior to the ventricular arrhythmia. As discussed above, the absence of SNCL changes or the presence of SNCL lengthening correlates with a more rapid drop in blood pressure and shortened time to syncope compared to SNCL shortening. In this case, the method delivers shock therapy to the patient to treat the ventricular arrhythmia in step 1460*b* without attempting ATP first. The shock therapy may include one of defibrillation and electrical cardioversion.

The ranges shown in FIG. 14 for the change in SNCL are exemplary. For example, the method may proceed to step 1450*a* when the percent SNCL change % ΔSNCL is less than a negative value, e.g., less than −10%, and proceed to step 1450*b* when % ΔSNCL is above this value. In other words, the boundary between whether to deliver ATP or shock therapy to the patient may be a value other than zero. In general, the method may proceed to step 1450*a* when the change in SNCL is within a first range and proceed to step 1450*b* when the change in SNCL is within a second range, different from the first range. The same applies to steps 1452*a*, 142*b*, 1455*a* and 1455*b* discussed below.

In step 1440*b*, which corresponds to a ventricular arrhythmia cycle length of between 240 ms and 320 ms, the method determines a change in the SNCL between a time during the ventricular arrhythmia and a time prior to the onset of the ventricular arrhythmia. The change in the SNCL may be given as a percent SNCL change (%ΔSNCL), as discussed above.

When %ΔSNCL is less than zero, which corresponds to SNCL shortening, the method proceeds to step 1452*a*. In this case, the method may deliver ATP twice (ATP×2) to the patient to treat the ventricular arrhythmia in step 1462*a*. Each ATP may comprise a sequence of pulses (e.g., six, seven, eight, nine or ten pulses) with a CL≦88% of VA CL.

When %ΔSNCL is equal to or greater than zero, which corresponds to SNCL lengthening, the method proceeds to step 1452*b*. As discussed above, SNCL lengthening correlates with a shortened time to syncope compared to SNCL shortening, providing less time for ATP attempts before syncope. In the case, the method may deliver ATP once (ATP×1) to the patient to treat the ventricular arrhythmia in step 1462*b*. The ATP may comprise a sequence of pulses at 88% of VA CL. If the ATP fails, then shock therapy may be delivered to the patient.

In step 1440*c*, which corresponds to a ventricular arrhythmia cycle length of between 320 ms and 380 ms, the method determines a change in the SNCL between a time during the ventricular arrhythmia and a time prior to the onset of ventricular arrhythmia. The change in the SNCL may be given as a percent SNCL change (%ΔSNCL).

When %ΔSNCL is less than zero, which corresponds to SNCL shortening, the method proceeds to step 1455*a*. In this case, the method may deliver ATP four times (ATP×4) to the patient to treat the ventricular arrhythmia in step 1465*a*. Each of the first two ATPs may comprise a sequence of pulses (e.g., eight pulses) at 88% of VA CL and each of the last two ATPs may comprise a sequence of pulses (e.g., eight pulses) with a CL≦88% of VA CL.

When %ΔSNCL is equal to or greater than zero, which corresponds to SNCL lengthening, the method proceeds to step 1455*b*. As discussed above, SNCL lengthening correlates with a shortened time to syncope compared to SNCL shortening, providing less time for ATP attempts before syncope. In this case, the method may deliver ATP twice (ATP×2) to the patient to treat the ventricular arrhythmia in step 1465*b*.

Thus, the method may examine both the ventricular arrhythmia cycle length and changes in the SNCL in determining the appropriate therapy to treat ventricular arrhythmia. First, the method may examine the ventricular arrhythmia cycle length and select a subset of possible therapies based on the cycle length. For example, when the cycle length is less than 240 ms, the method in FIG. 14 selects the subset of APT×1 (one ATP attempt) and shock therapy as possible therapies. When the cycle length is between 240 ms and 320, the method in FIG. 14 selects the subset ATP×2 (two ATP attempts) and APT×1. Those skilled in the art will appreciate that the cycle length ranges and possible therapies illustrated in FIG. 14 are exemplary. Second, the method selects one of the therapies from the subset of therapies based on the change in the SNCL between a time prior to the onset of the ventricular arrhythmia and a time during the ventricular arrhythmia. In one embodiment, the method selects the therapy to treat the ventricular arrhythmia based on whether the SNCL shortens (e.g., %ΔSNCL<0) or the SNCL lengthens (e.g., %ΔSNCL≧0) during the ventricular arrhythmia compared to the time prior to the ventricular arrhythmia.

Figure 15:
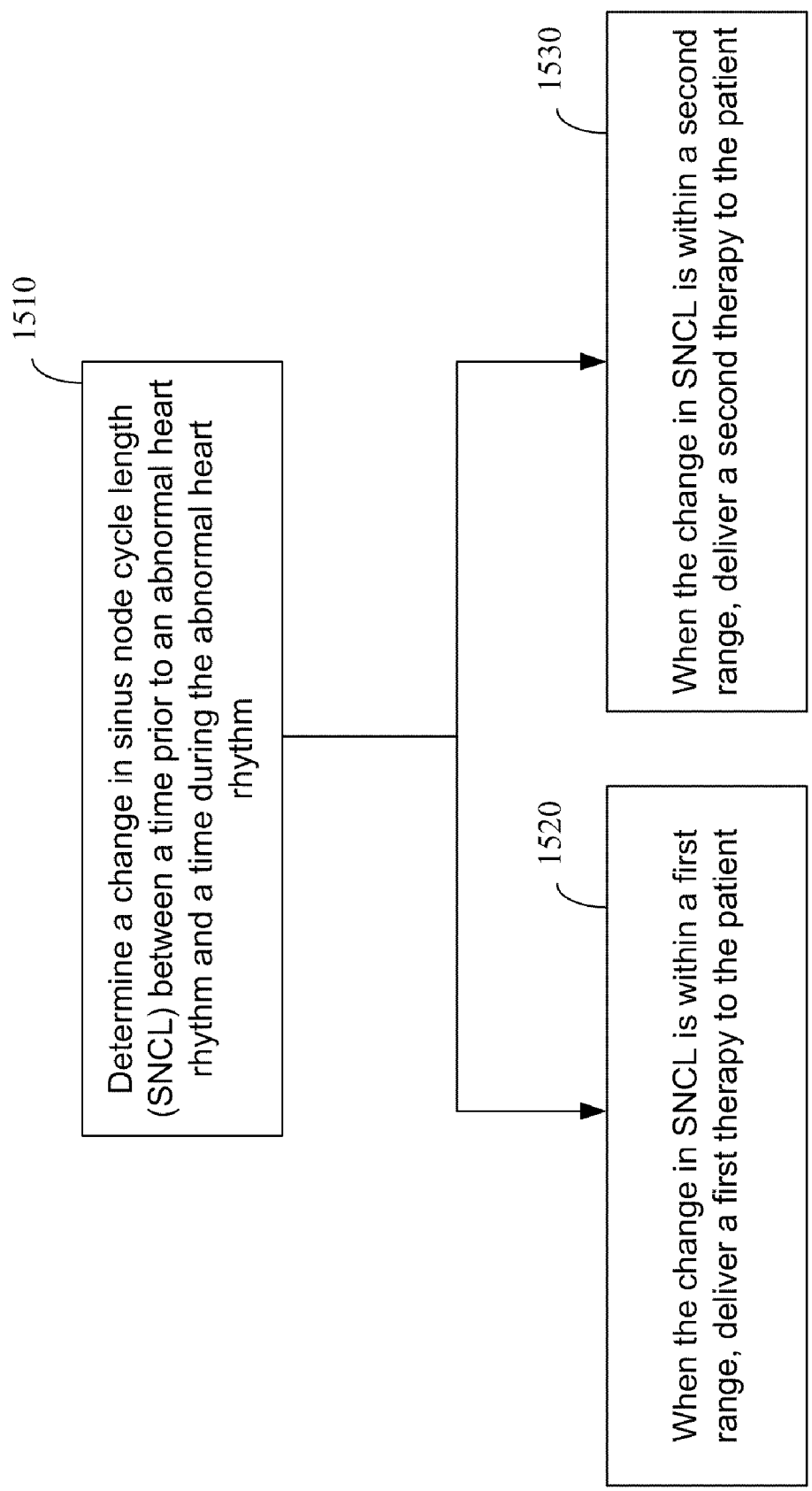
FIG. 15 is a flowchart of a method for treating an abnormal heart rhythm according to an embodiment of the present invention.

FIG. 15 is a flowchart of a method for treating an abnormal heart rhythm based on a change in SNCL according to an embodiment of the present invention. The abnormal heart rhythm may be ventricular arrhythmia. The abnormal heart rhythm may be detected by an ICD monitoring electrical activity of the heart. In step 1510, the method determines a change in the SNCL between a time prior to the abnormal rhythm and a time during the abnormal heart rhythm. When the change in SNCL is within a first range, the method delivers a first therapy to the patient in step 1520. For example, the first range may correspond to lengthening of the SNCL during the abnormal heart rhythm compared to the time prior to the abnormal heart rhythm. When the change in SNCL is within the second range, the method delivers a second therapy, different from the first therapy, to the patient in step 1530. For example, the second range may correspond to shortening of the SNCL during the abnormal heart rhythm compared to the time prior to the abnormal heart rhythm.

The methods according to various embodiments of the present invention may be performed by an ICD implanted in the patient. For example, an ICD capable of delivering both ATP and shock therapy to a patient may be programmed to perform the methods according to various embodiments of the present invention. The ICD may comprise the determining module and delivery module shown in FIG. 13.

The determining module may comprise electrodes implanted in the patient for sensing electrical activity of the heart. The electrodes may include one or more electrodes positioned in or near the upper and/or lower chambers of the heart. The determining module may also include a processor for analyzing electrical measurements from the one or more electrodes and a machine-readable storage device for storing the measurements and one or more programs executed by the processor for performing the methods according to various embodiments of the invention. The machine-readable storage device may include RAM, ROM, flash memory or a combination thereof. In one embodiment, the determining module may continuously monitor the SNCL and store a moving window of the SNCL in memory (e.g., the SNCL in the last 5 seconds). When a ventricular arrhythmia or other abnormal heart rhythm is detected, the determining module can retrieve the stored SNCL to determine the SNCL prior to the onset of the ventricular arrhythmia. The determining module may then determine the change in the SNCL between the time prior to and during the ventricular arrhythmia. In one embodiment, the determining module may compute a first mean SNCL within a first window (e.g., 5 seconds) prior to the onset of the ventricular arrhythmia and compute a second mean SNCL within a second window (e.g., 5 seconds) after the onset of the ventricular arrhythmia. The determining module may then determine the change in SNCL based on the first and second mean SNCL.

The delivery module may include one or more electrodes implanted in the patient for delivering ATP or shock therapy to the patient. For example, the delivery module may include one or more electrodes implanted in or near one or both ventricles of the heart to deliver ATP or shock therapy to terminate ventricular arrhythmia. The delivery module may share one or more electrodes with the determining module. The delivery module may also include one or more electrical signal generators to generate electrical signals for the ATP or shock therapy. The delivery module may also include the same processor as the determining module or a different processor and the same memory as the determining module or a different memory. The delivery module may be programmed to receive the change in SNCL from the determining module and to deliver one of a plurality of different therapies to the patient based on the change in the SNCL. For example, the delivery module may be programmed to deliver a first therapy when the change in SNCL indicates SNCL lengthening during an abnormal heart rhythm compared to the time prior to the abnormal heart rhythm, and to deliver a second therapy, different from the first therapy, to the patient when the change in SNCL indicates SNCL shortening during the abnormal heart rhythm compared to the time prior to the abnormal heart rhythm.

Although preferred embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above.

What is claimed is:

1. A method, of treating a ventricular arrhythmia, comprising:
    determining occurrence of a ventricular arrhythmia comprising at least one of a ventricular tachycardia or a ventricular fibrillation;
    determining a change in a sinus node cycle length of a heart of a patient between a time 60 seconds or less prior to onset of the ventricular arrhythmia and a time during the ventricular arrhythmia;
    when the change in the sinus node cycle length is within a first range corresponding to lengthening of the sinus node cycle length during the ventricular arrhythmia, delivering a first electrical therapy to the patient for treating the ventricular arrhythmia; and
    when the change in the sinus node cycle length is within a second range corresponding to shortening of the sinus node cycle length during the ventricular arrhythmia, delivering a second electrical therapy to the patient for treating the ventricular arrhythmia, wherein the first electrical therapy is different from the second electrical therapy.

2. The method of claim 1, wherein the first electrical therapy comprises at least one of defibrillation or electrical cardioversion, and the second electrical therapy comprises anti-tachycardia pacing.

3. The method of claim 1, wherein the first electrical therapy comprises a first number of anti-tachycardia pacing (ATP) attempts, and the second electrical therapy comprises a second number of ATP attempts, the second number being greater than the first number.

4. The method of claim 1, wherein each of the ATP attempts comprises a sequence of pulses delivered to one or both ventricles of the patient.

5. The method of claim 1, wherein the determining the change in the sinus node cycle length comprises:
    determining a first mean sinus node cycle length within a first time window prior to the onset of the ventricular arrhythmia;
    determining a second mean sinus node cycle length within a second time window from the onset of the ventricular arrhythmia; and
    determining the change in the sinus node cycle length based on the first and second mean sinus node cycle lengths.

6. The method of claim 1, wherein the determining and the delivering are performed by a device implanted in the patient.

7. The method of claim 1, wherein the sinus node cycle length at the time prior to onset is measured during 5 seconds.

8. The method of claim 7, wherein the 5 seconds immediately precedes onset of the abnormal heart rhythm.

9. The method of claim 1, wherein the sinus node cycle length at the time during the abnormal heart rhythm is measured during 10 seconds or less.

10. The method of claim 9, wherein the 10 seconds or less immediately precedes application of the first or second therapy.

11. A method, of treating an abnormal heart rhythm, comprising:
    determining occurrence of an abnormal heart rhythm comprising at least one of a ventricular tachycardia or a ventricular fibrillation;
    determining a change in a parameter indicative of a sinus node cycle length of a heart of a patient from a time 60 seconds or less prior to onset of the abnormal heart rhythm to a time during the abnormal heart rhythm;
    when the change in the parameter indicative of the sinus node cycle length is greater than a threshold value, delivering a first electrical therapy to the patient for treating the abnormal heart rhythm; and
    when the change in the parameter indicative of the sinus node cycle length is less than the threshold value, delivering a second electrical therapy to the patient for treating the abnormal heart rhythm, wherein the first electrical therapy is different from the second electrical therapy.

12. The method of claim 11, wherein the first electrical therapy comprises at least one of defibrillation or electrical cardioversion, and the second electrical therapy comprises anti-tachycardia pacing.

13. The method of claim 11, wherein the first electrical therapy comprises a first number of anti-tachycardia pacing (ATP) attempts, and the second electrical therapy comprises a second number of ATP attempts, the second number being greater than the first number.

14. The method of claim 11, wherein the determining and the delivering are performed by a device implanted in the patient.

15. An implantable cardiac device, for treating an abnormal heart rhythm, comprising:
 a determining module that (i) determines occurrence of an abnormal heart rhythm comprising at least one of a ventricular tachycardia or a ventricular fibrillation and (ii) determines a change in a parameter indicative of a sinus node cycle length of a heart of a patient from a time 60 seconds or less prior to onset of the abnormal heart rhythm to a time during the abnormal heart rhythm; and
 a delivery module, programmed to deliver a first electrical therapy for treating the abnormal heart rhythm to the patient when the change in the parameter is greater than a threshold value, and to deliver a second electrical therapy for treating the abnormal heart rhythm, different from the first electrical therapy, to the patient when the change in the parameter is less than the threshold value.

16. The device of claim 15, wherein the first electrical therapy comprises at least one of defibrillation or electrical cardioversion, and the second electrical therapy comprises anti-tachycardia pacing.

17. The device of claim 15, wherein the first electrical therapy comprises a first number of anti-tachycardia pacing (ATP) attempts, and the second electrical therapy comprises a second number of ATP attempts, the second number being greater than the first number.

18. A method, of treating an abnormal heart rhythm, comprising:
 determining occurrence of an abnormal heart rhythm comprising at least one of a ventricular tachycardia or a ventricular fibrillation;
 determining a change in a parameter indicative of a sinus node cycle length of a heart of a patient from a time 60 seconds or less prior to onset of the abnormal heart rhythm to a time during the abnormal heart rhythm; and
 selecting, based on the change in the parameter indicative of the sinus node cycle length, at least one of a first electrical therapy or a second electrical therapy for treatment of the abnormal heart rhythm, the first electrical therapy being selected when the change in the parameter is greater than a threshold value and the second electrical therapy being selected when the change in the parameter is less than the threshold value.

19. The method of claim 18, wherein the sinus node cycle length at the time prior to onset is measured during 5 seconds.

20. The method of claim 19, wherein the 5 seconds immediately precedes onset of the abnormal heart rhythm.

21. The method of claim 18, wherein the sinus node cycle length at the time during the abnormal heart rhythm is measured during 5 seconds.

22. The method of claim 21, wherein the 5 seconds immediately precedes application of the first or second therapy.

\* \* \* \* \*